US010703777B2

(12) United States Patent
Kirshenbaum et al.

(10) Patent No.: US 10,703,777 B2
(45) Date of Patent: Jul. 7, 2020

(54) MINIATURE PROTEIN SCAFFOLDS AND METHODS FOR USE THEREOF

(71) Applicant: New York University, New York, NY (US)

(72) Inventors: Kent Kirshenbaum, New York, NY (US); Timothy W. Craven, Randolph, NJ (US); Richard Bonneau, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 15/879,872

(22) Filed: Jan. 25, 2018

(65) Prior Publication Data

US 2018/0230183 A1    Aug. 16, 2018

Related U.S. Application Data

(60) Provisional application No. 62/450,296, filed on Jan. 25, 2017.

(51) Int. Cl.
*C07K 7/08* (2006.01)
*G01N 33/68* (2006.01)

(52) U.S. Cl.
CPC .......... *C07K 7/08* (2013.01); *G01N 33/6845* (2013.01); *C07K 2299/00* (2013.01); *C07K 2318/10* (2013.01); *C07K 2318/20* (2013.01); *G01N 2500/02* (2013.01)

(58) Field of Classification Search
None
See application file for complete search history.

(56) References Cited

PUBLICATIONS

Craven et al. ("A Miniature Protein Stabilized by a Cation-π Interaction Network," J. Am. Chem. Soc. 2016, 138, 1543-1550) (Year: 2016).*
Appelbaum, J . M.; LaRochelle, J. R.; Smith, B. A; Balkin, D. M.; Holub, J.M.; Schephartz, A Chem. Biol. 2012, 19, 819-830, "Arginine Topology Controls Escape of Minimally Cationic Proteins from Early Endosomes to the Cytoplasm".
Smith, B.; Daniels, D. S.; Coplin, A; Jordan, G.; McGregor, L.; Schepartz, A J. Am. Chem. Soc. 2008, 130, 2948-2949, "Minimally Cationic Cell-Permeable Miniature Proteins via α-Helical Arginine Display".
Li, M.; Tao, Y.; Shu, Y.; LaRochelle, J. R.; Steinauer, A; Thompson, D.; Schepartz, A; Chen, Z.-Y.; Liu, D. J. Am. Chem. Soc. 2015, 137, 14084-14093, "Discovery and Characterization of a Peptide That Enhances Endosomal Escape of Delivered Proteins in Vitro and in Vivo".
Kortemme, T.; Ramirez-Alvarado, M.; Serrano, L. Science 1998, 281, 253-256, "Design of a 20-Amino Acid, Three-Stranded β-Sheet Protein".
Struthers, M. D. ; Cheng, R. P.; Imperiali, B. Science 1996, 271, 342-345, "Design of a Monomeric 23-Residue Polypeptide with Defined Tertiary Structure".
Neidigh,. J. W.; Fesinmeyer, R. M.; Andersen, N. H. Nat. Struct. Biol. 2002, 9, 425-430, "Designing a 20-residue protein".
Honda, S.; Yamasaki, K.; Sawada, Y.; Morii, H. Structure 2004, 12, 1507-1518, "10 Residue Folded Peptide Designed by Segment Statistics".
Cochran, A. G.; Skelton, N. J .; Starovasnik, M. A. Proc. Natl. Acad. Sci. U. S. A. 2001 , 98, 5578-5583, "Tryptophan zippers: Stable, monomeric β-hairpins".
Hodges, A. M.; Schepartz, A. J. Am. Chem. Soc. 2007, 129, 11024-11025, "Engineering a Monomeric Miniature Protein".
Espinosa, J. F.; Gellman, S. H. Angew. Chem., Int. Ed. 2000, 39, 2330-2333, "A Designed β-Hairpin Containing a Natural Hydrophobic Cluster** ".
Ottesen, J. J.; Imperiali, B. Nat. Struct. Biol. 2001, 8, 535-539, "Design of a discretely folded mini-protein motif with predominantly β-structure".
Kier, B. L; Andersen, N. H.J. Am. Chem. Soc. 2008, 130, 14675-14683, "Probing the Lower Size Limit for Protein-like Fold Stability: Ten-residue Microproteins Greater than 97% Folded in Water at 280K".
Dougherty, D. A. Science 1996, 271, 163-168, "Cation-π Interactions in Chemistry and Biology: A New View of Benzene, Phe, Tyr, and Trp".
Gallivan, J.P.; Dougherty, D. A. Proc. Natl. Acad. Sci. U. S. A. 1999, 96, 9459-9464, "Cation-π interactions in structural biology".
Trotta, C.R.; Paushkin, S. V. ; Patel, M.; Li, H.; Peitz, S. W. Nature 2006, 441, 375-377, "Cleavage of pre-tRNAs by the splicing endonuclease requires a composite active site".
Xiu, X.; Puskar, N. L.; Shanate, J.A. P.; Lester, H. A.; Dougherty, D. A. Nature 2009, 458, 534-537, "Nicotine binding to brain receptors requires a strong cation-π interaction".
Dagil, R. ; Knudsen, M. J .; Olsen, J. G.; O'Shea, C.; Franzmann, M.; Goffin, V. ; Teilum, K.; Breinholt, J .; Kragelund, B. B. Structure 2012, 20, 270-282, "The WSXWS Motif in Cytokine Receptors Is a Molecular Switch Involved in Receptor Activation: Insight from Structures of the Prolactin Receptor".
Hilton, D. J.; Watowich, S. S.; Katz, L.; Lodish, H.F. J. Biol. Chem. 1996, 271, 4699-4708, "Saturation Mutagenesis of the WSXWS Motif of the Erythropoietin Receptor".
Gallivan, J.P.; Dougherty, D. A. J. Am. Chem. Soc. 2000, 122, 870-874, "A Computational Study of Cation-π Interactions vs Salt Bridges in Aqueous Media: Implications for Protein Engineering".
Shi, Z.; Olson, C.; Kallenbach, N. J. Am. Chem. Soc. 2002, 124, 3284-3291, "Cation-π Interaction in Model α-Helical Peptides".
Tatko, C. D .; Waters, M. L. Protein Sci. 2003, 12, 2443-2452, "The geometry and efficacy of cation-π interactions in a diagonal position of a designed β-hairpin".
Hughes, R. M.; Waters, M. L. J. Am. Chem. Soc. 2006, 128, 12735-12742, "Arginine Methylation in a β-Hairpin Peptide: Implications for Arg-π Interactions, ΔC p°, and the Cold Denatured State".

(Continued)

*Primary Examiner* — Christina Bradley
(74) *Attorney, Agent, or Firm* — Hoffmann & Baron, LLP

(57) ABSTRACT

Miniature protein scaffolds and compositions thereof (e.g., vaccine formulations) and methods of using same are described herein. In a particular embodiment, the miniature protein scaffold comprises an isolated β-strand connected via a loop to a left-handed poly proline type-II (PPII) helix formed in the absence of proline residues.

15 Claims, 19 Drawing Sheets

Specification includes a Sequence Listing.

(56) References Cited

PUBLICATIONS

Prajapati, R. S.; Sirajuddin, M.; Durani, V.; Sreeramulu, S.; Varadarajan, R. Biochemistry 2006, 45, 1500-15010, "Contribution of Cation-π Interactions to Protein Stability†".

Chakravarty, S.; Varadarajan, R. Biochemistry 2002, 41, 8152-8161, "Elucidation of Factors Responsible for Enhanced Thermal Stability of Proteins: A Structural Genomics Based Study†".

Crooks, G. E.; Hon, G.; Chandonia, J.M.; Brenner, S. E. Genome Res. 2004, 14, 1188-1190, "WebLogo: A Sequence Logo Generator".

Bravo, J.; Staunton, D.; Heath, J.; Jones, E . EMBO J. 1998, 17, 1665-1674, "Crystal structure of a cytokine-binding region of gp130".

Wang, X.; Rickert, M.; Garcia, K. Science 2005, 310, 1159-1163, "Structure of the Quaternary Complex of Interleukin-2 with Its α, β, and γc Receptors".

Laporte, S. L.; Juo, Z. S.; Vaclavikova, J.; Colf, L. A; Qi, X.; Heller, N. M.; Keegan, A D.; Garcia, K. C. Cell 2008, 132, 259-272, "Molecular and Structural Basis of Cytokine Receptor Pleiotropy in the Interleukin-4/13 System".

Aritomi, M.; Kunishima, N.; Okamoto, T.; Kuroki, R.; Ota, Y.; Morikawa, K. Nature 1999, 401, 713-717, "Atomicstructure of the GCSF-receptor complex showing a new cytokine-receptor recognition scheme".

Syed, R. S.; Reid, S. W.; Li, C.; Cheetham, J. C.; Aoki, K. H.; Liu, B.; Zhan, H.; Osslund, T. D.; Chirino, A. J.; Zhang, J.; Finer-Moore, J.; Elliott, S.; Sitney, K.; Katz, B. A; Matthews, D. J.; Wendoloski, J. J.; Egrie, J.; Stroud, R. M. Nature 1998, 395, 511-516, "Efficiency of signalling through cytokine receptors depends critically on receptor orientation".

Tamada, T.; Honjo, E.; Maeda, Y.; Okamoto, T.; Ishibashi, M.; Tokunaga, M.; Kuroki, R. Proc. Natl. Acad. Sci. U. S. A. 2006, 103, 3135-3140, "Homodimeric cross-over structure of the human granulocyte colony-stimulating factor (GCSF) receptor signaling complex".

Skiniotis, G.; Lupardus, P.; Martick, M.; Walz, T.; Garcia, K. C. Mol. Cell 2008, 31, 737-748, "Structural Organization of a Full-Length gp130/LIF-R Cytokine Receptor Transmembrane Complex".

Rossjohn, J.; McKinstry, W. J.; Woodcock, J.M.; McClure, B. J.; Hercus, T. R.; Parker, M. W.; Lopez, AF.; Bagley, C. J. Blood 2000, 95, 2491-2498, "Structure of the activation domain of the GM-CSF/IL-3/IL-5 receptor common β-chain bound to an antagonist".

Broutin, I.; Jomain, J.; Tallet, E.; Agthoven, J.; Raynal, B.; Hoos, S.; Kragelund, B. B.; Kelly, P. A; Ducruix, A; England, P.; Goffin, V. J. Biol. Chem. 2010, 285, 8422-8433,"Crystal Structure of an Affinity-matured Prolactin Complexed to Its Dimerized Receptor Reveals the Topology of Hormone Binding Site 2*□S".

Lupardus, P. J.; Birnbaum, M.; Garcia, K. Structure 2010, 18, 332-342, "Molecular Basis for Shared Cytokine Recognition Revealed in the Structure of an Unusually High Affinity Complex between IL-13 and IL-13Rα2".

Varghese, J. N.; Moritz, R. L.; Lou, M. Z.; Donkelaar, A; Ji, H.; Ivancic, N.; Branson, K. M.; Hall, N. E.; Simpson, R. J. Proc. Natl. Acad. Sci. U. S. A. 2002, 99, 15959-15964, "Structure of the extracellular domains of the human interleukin-6 receptor α-chain".

Huyton, T.; Zhang, J. G.; Luo, C. S.; Lou, M. Z.; Hilton, D. J.; Nicola, N. A; Garrett, T. P. Proc. Natl. Acad. Sci. U. S. A. 2007, 104, 12737-12742, "An unusual cytokine:lg-domain interaction revealed in the crystal structure of leukemia inhibitory factor (LIF) in complex with the LIF receptor".

Patino, E.; Kotzsch, A.; Saremba, S.; Nickel, J.; Schmitz, W.; Sebald, W.; Mueller, T. D . Structure 2011, 19, 1864-1875, "Structure Analysis of the IL-5 Ligand-Receptor Complex Reveals a Wrench-like Architecture for IL-5Rα".

Hamming, 0. J.; Kang, L.; Svensson, A.; Karlsen, J. L.; Rahbek-Nielsen, H.; Paludan, S. R.; Hjorth, S. A.; Bondensgaard, K.; Hartmann, R. J. Biol. Chem. 2012, 287, 9454-9460. "Crystal Structure of Interleukin-21 Receptor (IL-21R) Bound to IL-21 Reveals That Sugar Chain Interacting with WSXWS Motif is Integral Part of IL-21R*□S".

Carpenter, B.; Hemsworth, G. R.; Wu, Z.; Maamra, M.; Strasburger, C. J.; Ross, R. J.; Artymiuk, P . J. Structure 2012, 20, 487-497, "Structure of the Human Obesity Receptor Leptin-Binding Domain Reveals the Mechanism of Leptin Antagonism by a Monoclonal Antibody".

Dunbrack, R. L.; Karplus, M. A. J. Mol. Biol. 1993, 230, 543-574, "Backbone-dependent Rotamer Library for Proteins, Application to Side-chain Prediction".

Leaver-Fay, A.; et al. An Object-Oriented Software Suite for the Simulation and Design of Macromolecules. In Methods in Enzymology; Johnson, M. L, Brand, L., Eds.; Computer Methods, Part C; Academic Press: New York, 2011; vol. 487, pp. 545-574, ROSETTA3: "An Object-Oriented Software 'Suite for the Simulation and Design of Macromolecules".

Vuister, G. W.; Bax, A. J. Am. Chem. Soc. 1993, 115, 7772-7777, "Measurement of four-bond HN-Hα J-couplings in staphylococcal nuclease".

Schwieters, C. D.; Kuszewski, J. J.; Tjandra, N.; Clore, G. M. J. Magn. Reson. 2003, 160, 66-74, "The Xplor-NIH NMR molecular structure determination package".

Schwieters, C. D.; Kuszewski, J. J.; Clore, G. M. Prog. Nucl. Magn. Reson. Spectrosc. 2006, 48, 47-62, "Using Xplor-NIH for NMP molecular structure determination".

Kelly, S. M.; Price, N. C. Curr. Protein Pept. Sci. 2000, 4, 349-384, "The Use of Circular Dichroism in the Investigation of Protein Structure and Function".

Horng, J.C.; Raines, R. T. Protein Sci. 2006, 1, 74-83, "Stereoelectronic effects on polyproline conformation".

Chellgren, B. W.; Creamer, T. P. Biochemistry 2004, 43, 5864-5869, "Short Sequences of Non-Proline Residues Can Adopt the Polyproline II Helical Conformation†".

Krimm, S.; Tiffany, M. L., Isr. J. Chem. 1974, 12, 189-200, "The Circular Dichroism Spectrum and Structure of Unordered Polypeptides and Proteins".

Brown, A. M.; Zondlo, N . J. Biochemistry 2012, 51, 5041-5051, "A Propensity Scale for Type II Polyproline Helices (PPII): Aromatic Amino Acids in Proline-Rich Sequences Strongly Disfavor PPII Due to Proline-Aromatic Interactions".

Zheng, J.; Baghkhanian, A. M.; Nowick, J. S. J. Am. Chem. Soc. 2013, 135, 6846-6852, "A Hydrophobic Surface Is Essential to Inhibit the Aggregation of a Tau-Protein-Derived Hexapeptide".

Nguyen, J. T.; Turck, C. W.; Cohen, F. E.; Zuckermann, R. N .; Lim, W. A. Science 1998, 282, 2088-2092, "Exploiting the Basis of Proline Recognition by SH3 and WW Domains: Design of N-Substituted Inhibitors".

Bunagan, M. R.; Yang, X.; Saven, J. G.; Gai, F. J. Phys. Chem. B 2006, 110, 3759-3763, "Ultrafast Folding of a Computationally Designed Trp-Cage Mutant: Trp2-Cage†".

* cited by examiner

Fig. 3A
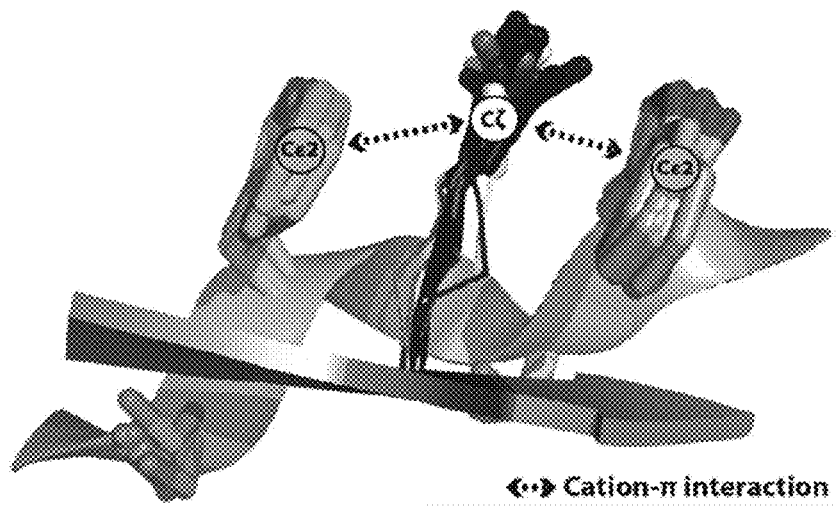
Fig. 3B
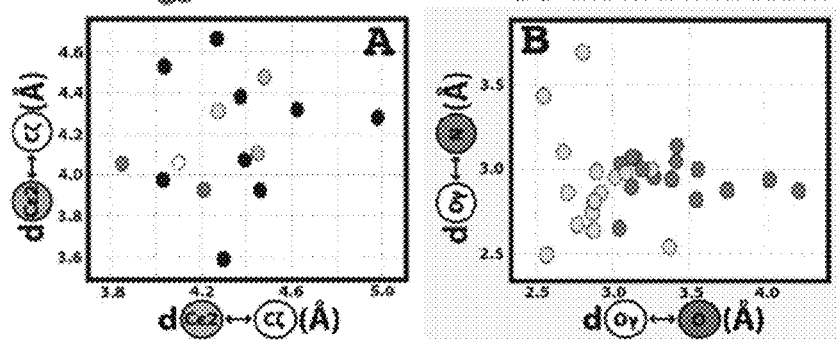
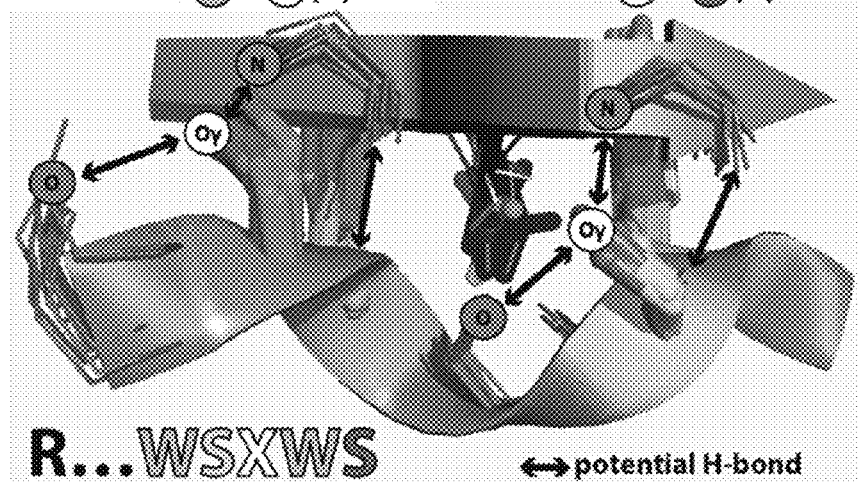

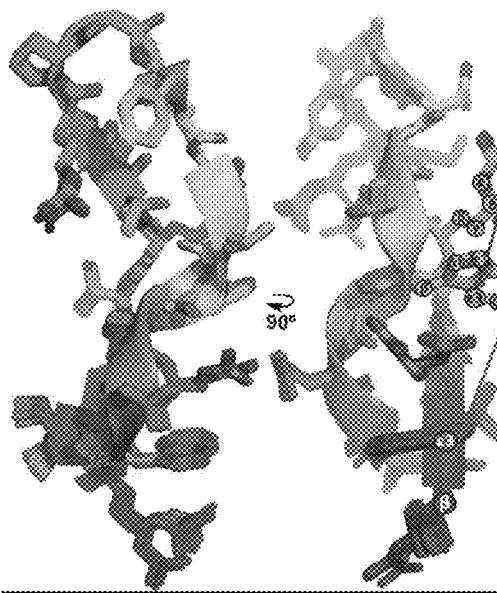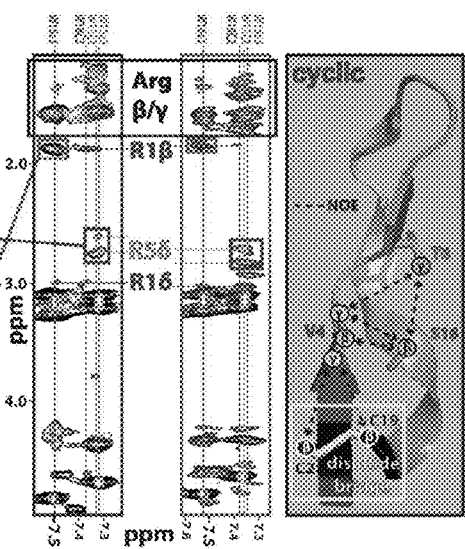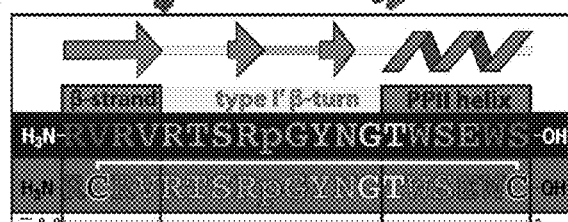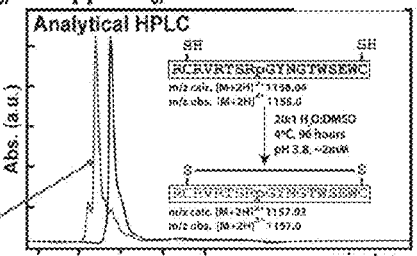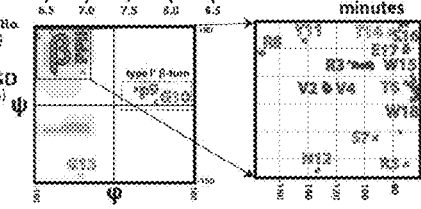
Fig. 5A
Fig. 5B
Fig. 5C
Fig. 5D
Fig. 5E
Fig. 5F

Fig. 7

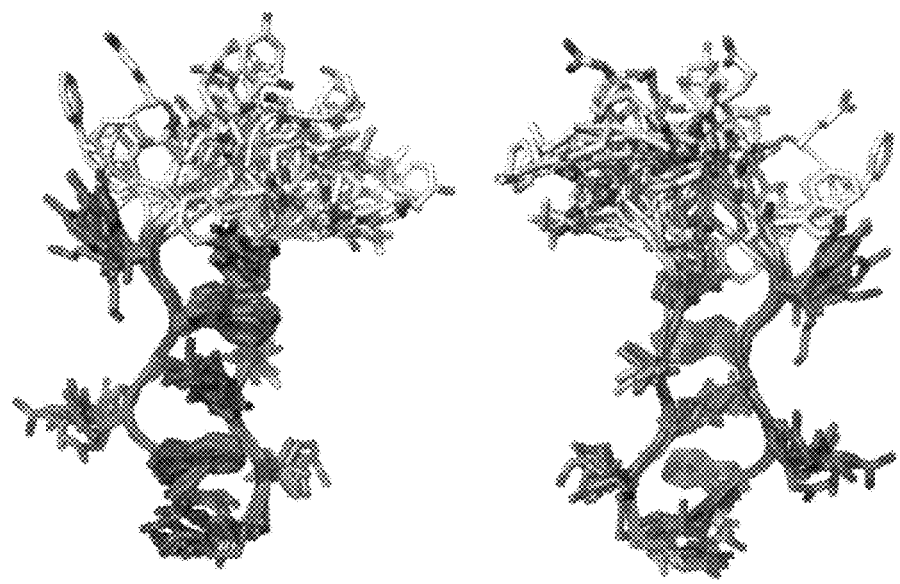

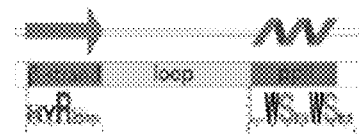

WSXWS motif

| UniprotID | PDBid | Chain | Residues | Sequence |
|---|---|---|---|---|
| P40189 | 1bqu | A | 160-196 | RIRCMKEDGKG....YWSDWS |
| P14784 | 2b5i | B | 181-196 | QVRVKPLQGEFT...TWSPWSQ |
| P31785 | 2b5i | C | 200-216 | RVRSRFNPLCGSAQ.HWSEWSR |
| P78552 | 3bpn | C | 311-331 | RIRVKTNELCYEDDKLWSNWSQ |
| P40223 | 1cd9 | B | 186-201 | QKRCIRSSLPG....FWSPWSP |
| P19235 | 1cn4 | A | 195-211 | AVRARMAEPSFGG..FWSEWSS |
| Q99062 | 2d9q | B | 283-298 | QIRCIRWPLSG....HWSDWSP |
| P40701 | 3e0g | A | 457-471 | RIRCSTETFW.....KWSKWSN |
| P32927 | 1egj | A | 411-426 | RVRVRTSRTGYNG..IWSEWSE |
| P05710 | 3ew3 | B | 181-196 | QTRCKPDHG......YWSRWSQ |
| Q14627 | 3lb6 | D | 307-326 | VVRSKVNIYCSDDG.IWSEWSD |
| P08887 | 1n26 | A | 272-286 | QLPAQEEFGQG....EWSEWSP |
| P40703 | 2q7n | A | 460-476 | RVRCSSKTFW.....KWSRWSD |
| Q01344 | 3qt2 | A | 287-306 | QVRAAYSSMCREAG.LWSEWSQ |
| Q9HBE5 | 3tgx | A | 180-196 | QVRASSMFGSSTQG.TWSEWSD |
| P48357 | 3v6o | A | 610-626 | QVRCKRLDGLG....YWSNWSN |

Figure 12
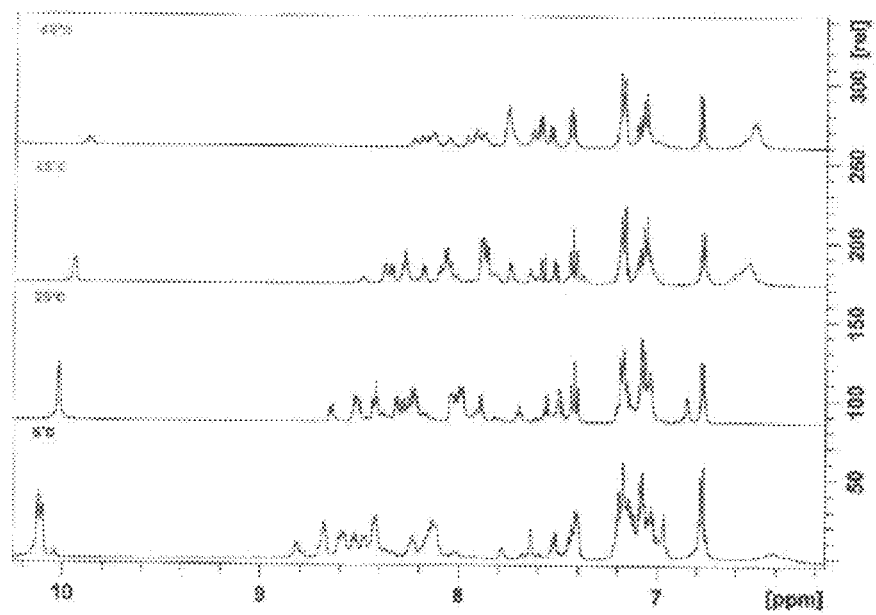
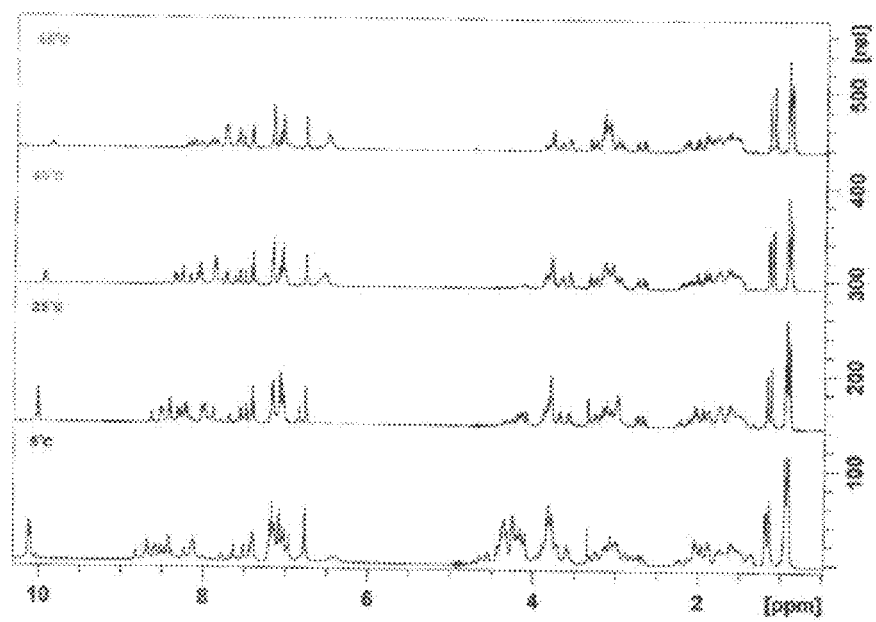

Figure 16
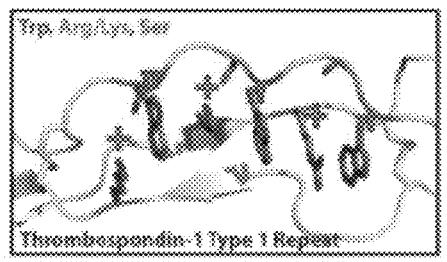
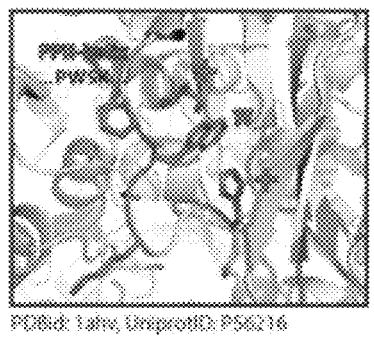
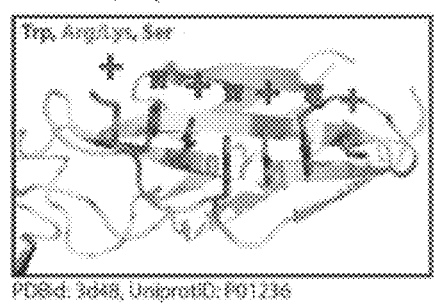
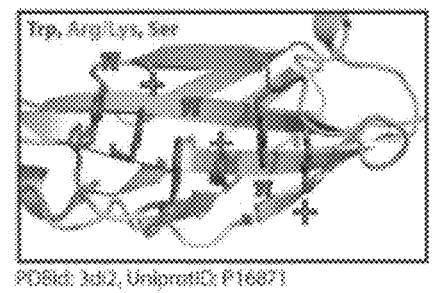
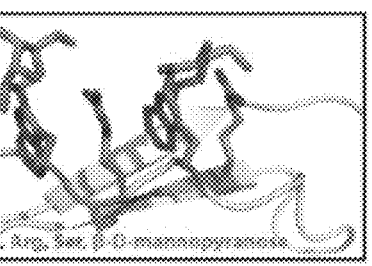
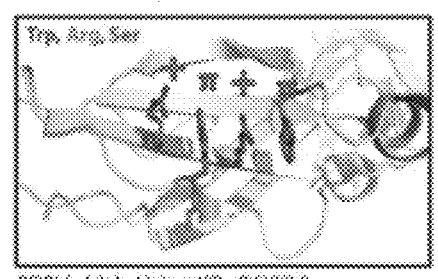
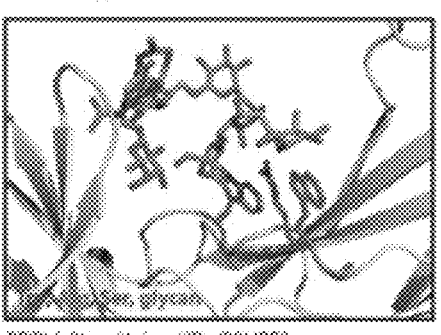

Figure 17-1

|  |  | R1 | | |
|---|---|---|---|---|
| Cζ | B-factor (Å²) | 11.92 | 57.81 | 24.23 |
| Nε | B-factor (Å²) | 9.66 | 56.10 | 23.41 |
| Cδ | B-factor (Å²) | 8.19 | 54.76 | 22.96 |
| Cγ | B-factor (Å²) | 9.86 | 54.90 | 22.88 |
| Cβ | B-factor (Å²) | 11.24 | 54.75 | 22.43 |
| Cα | B-factor (Å²) | 13.20 | 54.53 | 22.49 |
|  | Rotamer bin | 1 2 2 2 | 1 2 2 2 | 3 2 3 2 |
|  | Probability | 0.003096 | 0.003096 | 0.057772 |
|  | $X_4$ | −179.423 | 162.086 | 178.786 |
|  | $X_3$ | −174.663 | −169.134 | −46.164 |
|  | $X_2$ | 177.953 | −164.003 | −167.224 |
|  | $X_1$ | 65.187 | 71.085 | −64.229 |
|  | Res. No. | 180 | 200 | 311 |
|  | Chain | A | C | C |
|  | PDBID | 1BQU | 2B5I | 3BPN |

Figure 17-2

| | | | | | | | |
|---|---|---|---|---|---|---|---|
| 173.28 | 61.99 | 100.83 | | 9.40 | 50.55 | 54.41 | 29.12 | 7.46 |
| 173.43 | 62.88 | 100.99 | | 9.59 | 48.80 | 53.92 | 28.73 | 7.73 |
| 173.54 | 60.62 | 100.48 | | 8.10 | 49.10 | 52.43 | 27.71 | 2.00 |
| 173.61 | 57.59 | 98.91 | | 7.50 | 50.06 | 52.40 | 25.51 | 2.00 |
| 173.73 | 52.61 | 98.38 | | 6.16 | 50.74 | 53.33 | 24.20 | 2.00 |
| 173.72 | 53.20 | 98.58 | | 9.62 | 51.67 | 53.58 | 23.87 | 2.00 |
| 2 1 2 3 | 1 1 1 2 | 3 2 3 2 | | 1 2 2 2 | 1 2 2 2 | 1 2 2 2 | 1 2 2 2 | 1 2 3 2 |
| 0.002795 | 0.000067 | 0.057772 | R² | 0.003096 | 0.003096 | 0.003096 | 0.003096 | 0.000942 |
| -83.023 | 168.184 | -176.283 | | 173.032 | 178.069 | 178.651 | 168.944 | -134.646 |
| 174.513 | 72.796 | -54.860 | | -179.451 | -176.974 | 178.838 | -177.551 | -94.844 |
| 65.952 | 133.503 | -130.952 | | 175.494 | 176.038 | -171.881 | 175.580 | -143.243 |
| -162.354 | 27.436 | -43.718 | | 66.192 | 62.978 | 67.954 | 65.488 | 89.395 |
| 457 | 411 | 460 | | 182 | 183 | 202 | 313 | 190 |
| A | A | A | | A | B | C | C | B |
| 3EOG | 1EJG | 2Q7N | | 1BQU | 2B5I | 2B5I | 3BPN | 1CD9 |

Figure 17-3

| | | | | | | | | |
|---|---|---|---|---|---|---|---|---|
| 27.35 | 60.72 | 169.01 | 70.64 | 86.77 | 39.32 | 29.94 | 105.50 | 60.29 |
| 24.60 | 58.84 | 168.87 | 68.45 | 86.77 | 41.32 | 29.61 | 104.87 | 61.08 |
| 26.38 | 57.21 | 168.60 | 63.39 | 86.77 | 42.71 | 28.07 | 103.77 | 59.88 |
| 26.46 | 55.48 | 168.17 | 58.89 | 86.77 | 38.46 | 23.22 | 101.93 | 55.87 |
| 25.96 | 54.01 | 167.88 | 55.65 | 86.77 | 35.13 | 37.16 | 100.83 | 55.72 |
| 24.82 | 50.35 | 167.72 | 54.85 | 86.77 | 35.03 | 37.09 | 100.77 | 56.90 |
| 1 2 3 2 | 1 2 2 2 | 1 2 3 2 | 2 3 2 2 | 1 2 2 2 | 2 2 1 2 | 1 2 2 2 | 2 2 2 2 | 2 2 2 2 |
| 0.000942 | 0.003096 | 0.000942 | 0.000946 | 0.003096 | 0.051384 | 0.003096 | 0.092516 | 0.092516 |
| -140.685 | 169.199 | 173.805 | 178.476 | 146.309 | 156.360 | 177.619 | 163.936 | -166.311 |
| -46.572 | -156.925 | -73.617 | -119.462 | -141.954 | 71.622 | 177.613 | -174.314 | -164.680 |
| -143.217 | 168.273 | -174.678 | -118.684 | -179.720 | 155.589 | 172.290 | -137.195 | -163.033 |
| 83.946 | 62.445 | 52.482 | 135.343 | 77.069 | -145.025 | 68.393 | -172.106 | 163.936 |
| 197 | 285 | 459 | 413 | 183 | 309 | 274 | 462 | 289 |
| A | B | A | A | B | D | A | A | A |
| 1CN4 | 2D9Q | 3E0G | 1EGJ | 3EW3 | 3LB6 | 1N26 | 2Q7N | 3QT2 |

Figure 17-4

| 3TGX | 3V60 | ℞ | 2B51 | 1CN4 | 1EGJ |
|---|---|---|---|---|---|
| 47.91 | 37.51 | | 56.31 | 40.00 | 84.10 |
| 42.04 | 36.33 | | 55.69 | 35.47 | 83.87 |
| 39.35 | 34.51 | | 55.17 | 31.31 | 81.87 |
| 30.79 | 28.34 | | 56.84 | 31.78 | 80.27 |
| 24.25 | 29.36 | | 55.32 | 27.85 | 75.96 |
| 29.66 | 30.93 | | 55.39 | 26.48 | 73.33 |
| 1 2 2 2 | 1 2 2 2 | | 2 2 2 2 | 2 3 3 1 | 1 1 1 1 |
| 0.003096 | 0.003096 | | 0.092516 | 0.000164 | 0.000033 |
| −175.406 | 172.235 | | 177.470 | 71.249 | 88.317 |
| −179.169 | −174.765 | | −135.755 | −88.849 | 47.799 |
| 179.078 | 169.203 | | −157.274 | −136.082 | 127.950 |
| 70.785 | 66.879 | | −166.232 | −177.909 | 63.911 |
| 182 | 612 | | 204 | 199 | 415 |
| A | A | | C | A | A |
| 3TGX | 3V60 | | 2B51 | 1CN4 | 1EGJ |

MINIATURE PROTEIN SCAFFOLDS AND METHODS FOR USE THEREOF

RELATED APPLICATION

The present application claims priority under 35 U.S.C. § 119 of U.S. Provisional Application Ser. No. 62/450,296 filed Jan. 25, 2017. Applicants claim the benefit of the said U.S. provisional application, and the entire contents of said application are hereby incorporated herein by reference in their entirety.

GOVERNMENTAL SUPPORT

The research leading to the present invention was supported, at least in part, by grants from National Science Foundation, Award No. CHE-1507946). Accordingly, the Government has certain rights in the invention.

FIELD OF THE INVENTION

The present invention relates generally to miniature protein scaffolds and to compositions thereof and methods of using same as, for example, modulators of protein-protein interactions. Also encompassed herein are vaccine formulations comprising miniature protein scaffolds described herein. In a particular embodiment, the miniature protein scaffold comprises an isolated β-strand connected via a loop to a left-handed poly proline type-II (PPII) helix formed in the absence of proline residues. The invention also relates to compositions, formulations and methods for prevention and control of infectious diseases in humans and other mammals, birds, and reptiles susceptible to infection. Methods for inducing an immune response by administration of the miniature protein scaffolds and vaccine formulations comprising same are also provided.

BACKGROUND OF THE INVENTION

Miniature proteins afford an opportunity to isolate and evaluate noncovalent interactions that direct formation of the secondary and tertiary structures present in native proteins (1-9). Previous studies of mini-proteins have elucidated thermodynamic and kinetic features of folding that may become convoluted within the context of more complex protein architectures. Within miniproteins, the biophysical characteristics of particular interactions can therefore be elucidated more precisely. For example, the interactions between the guanidinium group of an arginine and the indole ring of tryptophan have now been extensively described (10-19). These so-called cation-π interactions are representative of stabilizing noncovalent contacts between positively charged (Arg, Lys, His) and aromatic (Phe, Tyr, Trp) side-chain functionalities (10), and provide distinctive contributions to protein structure and function (11-15). Several studies have investigated the energetic contributions of binary cation-π interactions (16-19). Their stabilizing strengths have been evaluated in the context of α-helices (−0.4 kcal/mol for residues positioned at i and i+4) (17) and β-sheets (−0.20 to −0.48 kcal/mol) (18, 19). Computational studies have estimated that the free energy of cation-π interactions can vary up to −5.5 kcal/mol (16). The strengths of cation-π interactions have been demonstrated to increase with temperature (20), establishing thermoprotective influences in thermophilic organisms (21).

The generation of miniprotein scaffolds that recapitulate protein domains and surfaces that are important in protein-protein interactions offers tools that can be used to investigate and modulate protein-protein interactions. The technical challenges involved in the design and generation of such miniprotein scaffolds has, however, impaired implementation of such reagents as targeted modulators of protein-protein interactions and protein domain mimics.

The citation of references herein shall not be construed as an admission that such is prior art to the present invention.

SUMMARY OF THE INVENTION

Results presented herein set forth a new miniature protein offering several distinctive features, which present new opportunities for future investigation in the context of an isolated well-folded system. These features include (1) an extensive cation-π interaction network, as opposed to a binary isolated interaction, (2) a novel miniature protein topology composed of a β-strand:loop:PPII-helix, (3) an isolated β-strand in a monomeric protein, which could offer opportunities for modulating β-sheet formation, and (4) a left-handed poly proline type-II helix formed in the absence of proline residues. The PPII-helix is stabilized through interdigitated tertiary contacts. This mode of PPII-helix stabilization in the context of a miniature protein could afford a new scaffold to emulate the i and i+3 PPII-helical-motif positions recognized by, for example, SH3 and WW protein domains. The continued engineering of miniature protein structures to contain β-strand (52), PPII (53, 54), or poly arginine (55-57) motifs may prove advantageous for developing a next generation of peptide therapeutics and biochemical tools. See also, Craven et al. (2016, J Am Chem Soc 138:1543-1550), and the supplementary materials available therewith, the entire contents of all of which is incorporated herein and made a part hereof, in its entirety.

In accordance with results presented herein, a miniature protein scaffold comprising or consisting of Arg Val Arg Val Arg Thr Ser Arg Xaa Gly Tyr Asn Gly Thr Trp Ser Glu Trp Ser is presented herein, wherein Xaa at position 9 is D-proline (D-Pro) and at least one of the arginine (Arg) at position 1, 5, or 8; the valine (Val) at position 2 or 4; the threonine (Thr) at position 6 or 14; the serine (Ser) at position 7, 16, or 19; the tyrosine (Tyr) at position 11; the asparagine (Asn) at position 12; the glycine (Gly) at position 13; and the glutamic acid (Glu) at position 17; is replaced by a different alpha amino acid.

In another embodiment, a miniature protein scaffold comprising or consisting of Arg Cys Arg Val Arg Thr Ser Arg D-Pro Gly Tyr Asn Gly Thr Trp Ser Glu Trp Cys is described herein, wherein at least one of the arginine (Arg) at position 1, 5, or 8; the valine (Val) at position 4; the threonine (Thr) at position 6 or 14; the serine (Ser) at position 7 or 16; the tyrosine (Tyr) at position 11; the asparagine (Asn) at position 12; the glycine (Gly) at position 13; and the glutamic acid (Glu) at position 17 is replaced by a different alpha amino acid. In a particular embodiment, thereof, the cysteines (Cys) at positions 2 and 19 are linked via a disulfide bridge.

In an aspect thereof, the different alpha amino acid is selected from tyrosine (Tyr), glycine (Gly), phenylalanine (Phe), methionine (Met), alanine (Ala), serine (Ser), isoleucine (Ile), leucine (Leu), threonine (Thr), valine (Val), proline (Pro), lysine (Lys), histidine (His), glutamine (Gln), glutamic acid (Glu), tryptophan (Trp), arginine (Arg), aspartic acid (Asp), asparagine (Asn), and cysteine (Cys). With respect to Pro, prolines bearing cationic substituents are also encompassed herein. Also envisioned herein are different amino acids comprising non-natural cationic side chains.

In a particular embodiment, the different alpha amino acid replacing Thr at position 14 is other than Ile. In another particular embodiment, at least one of the threonine (Thr) at position 14 and the glutamic acid (Glu) at position 17 is replaced by a different alpha amino acid. In a more particular embodiment, the Thr at position 14 is replaced by a different alpha amino acid. In yet another embodiment, the Glu at position 17 is replaced by a different alpha amino acid. In a still further embodiment, the Thr at position 14 and the Glu at position 17 are replaced by a different alpha amino acid.

In a particular embodiment, the asparagine (Asn) at position 12 and/or the glycine (Gly) at position 13 are replaced by a different alpha amino acid that represents a conservative amino acid substitution or are not replaced by a different alpha amino acid.

In another embodiment, at least one of the arginine (Arg) at position 1 and at position 5 is replaced by lysine (Lys) or histidine (His).

In a more particular embodiment, the miniature protein scaffold comprises Arg Val Arg Val Arg Thr Ser Arg D-Pro Gly Tyr Asn Gly Xaa Trp Ser Glu Trp Ser, wherein Xaa is Thr or Ile. In a still more particular embodiment thereof, Xaa is Thr.

In another particular embodiment, the miniature protein scaffold comprises Xaa Val Arg Val Xaa Thr Ser Arg D-Pro Gly Tyr Asn Gly Thr Trp Ser Glu Trp Ser, wherein Xaa at least one of position 1 and position 5 is lysine (Lys) or histidine (His). In a still more particular embodiment thereof, Xaa is Lys.

In yet another particular embodiment, the miniature protein scaffold comprises Arg Cys Arg Val Arg Thr Ser Arg D-Pro Gly Tyr Asn Gly Xaa Trp Ser Glu Trp Cys, wherein Xaa is Thr or Ile. In a still more particular embodiment thereof, Xaa is Thr.

In a further particular embodiment, the miniature protein scaffold comprises Xaa Cys Arg Val Xaa Thr Ser Arg D-Pro Gly Tyr Asn Gly Thr Trp Ser Glu Trp Cys, wherein Xaa at least one of position 1 and position 5 is lysine (Lys) or histidine (His). In a more particular embodiment thereof, Xaa is Lys.

Miniature protein scaffolds described herein may comprise at least one amino acid residue that is post-translationally modified. Post-translational modifications include, without limitation, glycosylation, phosphorylation, and methylation.

An immunogenic composition comprising a miniature protein scaffold described herein is also encompassed hereby. Such immunogenic compositions may comprise an immunologically effective amount of at least one adjuvant.

Also encompassed herein is a method for immunizing a host animal, the method comprising administering a miniature protein scaffold described herein or a composition thereof to the host animal. In an embodiment thereof, the host animal is a mammal (e.g., a domestic animal such as a dog, cat, pig, cow, horse, or goat). In a more particular embodiment thereof, the mammal is a primate and even more particularly may be a human.

Also encompassed herein is a method for disrupting protein-protein interactions, the method comprising: contacting a first protein and a second protein that interact via a fibronectin type III (Fn3) domain with a miniature protein scaffold described herein and detecting interactions between the first and second protein, wherein detecting a decrease in the interactions identifies the miniature scaffold as disruptive of the protein-protein interactions.

Also encompassed herein is a method for identifying an inhibitor of interactions of a first and second protein that interact via a fibronectin type III (Fn3) domain, the method comprising: contacting the first protein and second protein with a miniature protein scaffold described herein and detecting the interactions between the first and second protein, wherein detecting a decrease in the interactions identifies the miniature scaffold as an inhibitor the interactions.

In an aspect of the above methods, the interaction is measured by direct physical interaction, biological activity of either the first or second protein, or activity of biological pathway in which either of the first or second protein plays a role.

Other objects and advantages will become apparent to those skilled in the art from a review of the following description which proceeds with reference to the following illustrative drawings.

BRIEF DESCRIPTION OF THE DRAWINGS

FIGS. 3A and 3B. Characteristic cation-π interactions and hydrogen bonds in WSXWS motifs from proteins found in Table 1. (3A) Plot of the distance between the Cε2 indole carbon atoms of each tryptophan to the Cζ of the central arginine guanidinium group highlighted with space-filled atoms in black→white. Different shades of black→white identify arginine rotamers having similar side-chain dihedral angles (38). (FIG. 17 and Table S6). All values are <6.5 Å, a characteristic cutoff distance of cation-π interactions. (3B) Plot of the distance between the serine sidechain Oγ atom and the i−1 carbonyl oxygen (O) and the adjacent β-stand backbone amide nitrogen (N). Yellow and green circles correspond to the color-labeled serine residues found in the structural alignment. Black lines with arrows represent potential hydrogen bonds (H-bonds).

FIGS. 5A-5F. Structure determination of the TrpPlexus mini-protein. (5A) NMR ensemble alignment of the 25 lowest energy structures satisfying distance constraints (Tables S1-S3). Highlighted regions with arrows show long-range NOE cross-peaks of Hε3 and Hζ2 of W15 and W18. Tryptophan indole ring and arginine side-chain atom descriptors are labeled on W15 and W18 as well as R1 and R5. (5B) Cartoon of TrpPlexus secondary structure and color representations for each residue in panels A, D, and F. (5C) 3JHN-Hα scalar couplings and Hα CSDs of the linear (black) and cyclic disulfide-bridged (green) sequences at 25° C. (5D) (left panels) NOESY spectra (250 ms mixing time, 1.8 mM protein, 10:90 (v:v) D2O:H2O, 4° C.) with highlighted long-range NOE interactions present in the spectra for both linear and cyclic structures. (right panel) Unambiguous NOEs supporting the model of the disulfide-bridged cyclic structure (FIG. 15). (5E) Analytical HPLC trace monitoring the cyclization of the disulfide-bridged sequence. (5F) Ramachandran plot of the backbone dihedral angles of the NMR ensemble structures with labels corresponding to the φ and ψ angle domains of the secondary structures present. (inset) Highlights of the β-strand and PPII regions.

FIG. 7. Structural alignment of X-ray crystal structures of "WSXWS motifs" with sequences and identifiers (23-37).

Amide HN Temperature Coefficient Discussion:

The two conserved serine residues in the crystal structures of WSXWS motifs were all found to be hydrogen bonding to an adjacent β-stand in X-ray crystal structures. Quantification of this type of hydrogen bond in TrpPlexus is not trivial. No serine hydroxyls were found in the TOCSY spectra that correlated to serine residues of TrpPlexus. The temperature coefficients of the backbone HN of V2 and V4 are anomalously large in comparison to other values. These amides are hydrogen-bond donors to adjacent serine hydroxyls or the C-terminal carboxylate group of S19 in the NMR ensemble structures. The amide backbone temperature coefficients show that these protons are in an environment resulting in increased temperature coefficients relative to expected water exposed values of 7.1 ppb/K. Typically, amides that are protected from interactions with water have decreased temperature coefficients similar to that observed in TrpPlexus for the tyrosine phenol protected HN of G13. These increases have not been distinctly attributed to side-chain to backbone hydrogen-bond contacts but this result could lend evidence to this feature. Serine to alanine mutations in the Erythropoietin receptor's WSXWS motif were also found to result in global loss of structure (15). These results suggest serine residues are indeed critical for both folding of TrpPlexus and WSXWS motif containing domains.

Figure 11:
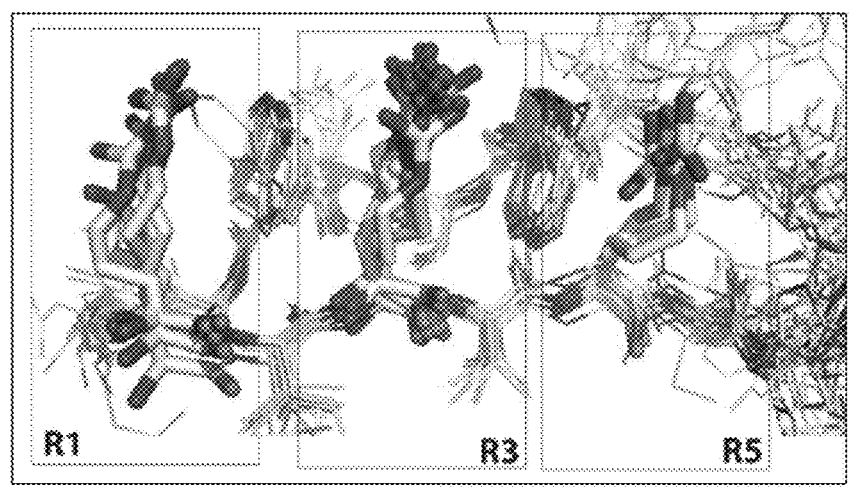

FIG. 11. Structural alignment (Cα) of 16 X-ray structures of "WSXWS motifs" with the core arginine residues highlighted (R1, R3, R5).

FIG. 12. 1D $^1$H NMR of TrpPlexus at 5° C., 25° C., 45° C. and 65° C. 1.8 mM in 10:90 (v:v) $D_2O:H_2O$.

Figure 13:
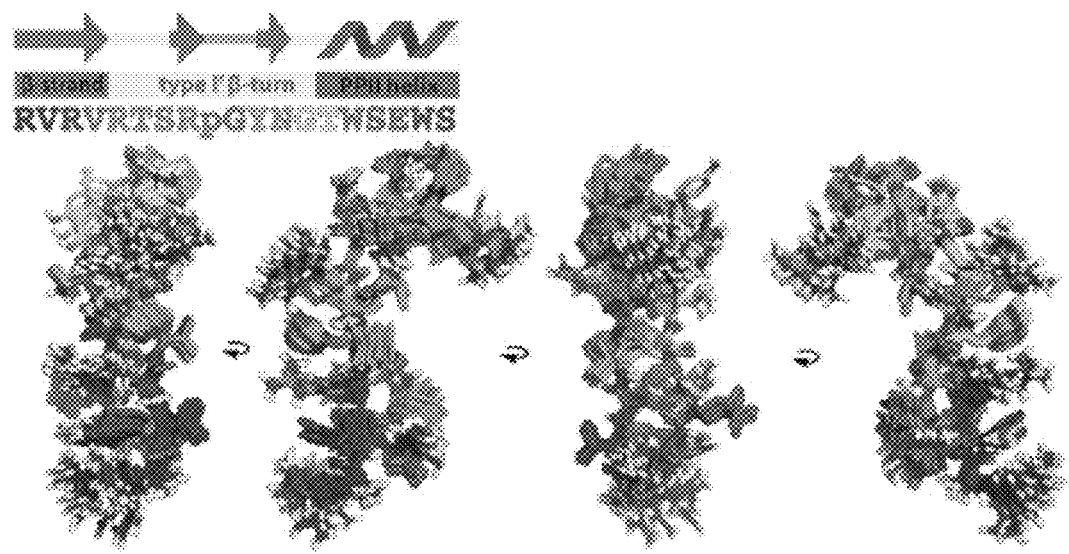

FIG. 13. Top 25 NMR solution structures of TrpPlexus determined using the xplor-NIH software package (41, 42) and identical structural constraints previously described.

Figure 14:
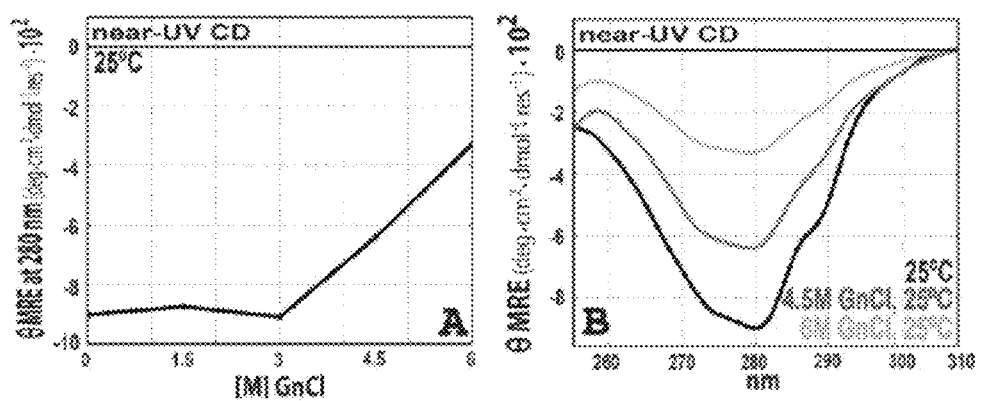

FIGS. 14A-14B. GnCl titrations and spectra of the cyclic TrpPlexus sequence. (14A) Near-UV CD MRE at 280 nm as a function of GnCl concentration. (14B) Near-UV CD spectra at varying concentrations of GnCl. CD spectra were collected using a 1 cm path length cell at 50 μM protein concentrations.

Figure 15:
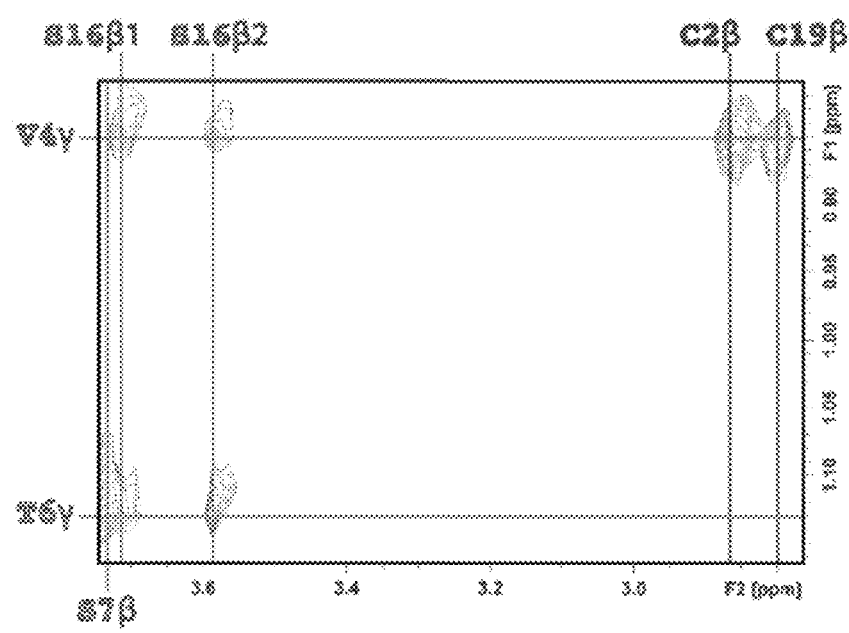

FIG. 15. Select NOEs observed in the $^1$H-$^1$H NOESY spectrum at 4C for the cyclic TrpPlexus sequence indicated by dashed lines in FIG. 5D (Right panel).

FIG. 16. A sampling of the variety of cation-π interaction networks found in X-ray crystal structures of protein domains. In cases where a tryptophan is followed by a serine, the serine is highlighted in green. In cases where a tryptophan residue is part of a cation-π interaction network while also displaying a c-linked sugar moiety, the sugar is highlighted in orange. The cationic functionalities can be seen highlighted with a blue (+) and the residues containing π-systems highlighted with a (π). Below the boxed structure are the PDBid and UniprotIDs for the structure and protein depicted.

FIG. 17-1, 17-2, 17-3, 17-4. Arginine rotamers for each position in the "WSXWS motif" along with rotamer probabilities, bin numbers (based upon the Dunbrack rotamer library nomenclature), and B-factors for each heavy atom in the side-chain. Rotamer probabilities are derived from backbone-dependent rotamer libraries based on the φ and ψ backbone angles of each individual residue occurrence in the crystal structures (38). Analysis of these rotamers can be seen in FIGS. 3A and 3B, and in the corresponding figure description presented hereinabove.

DETAILED DESCRIPTION

Figure 1A:
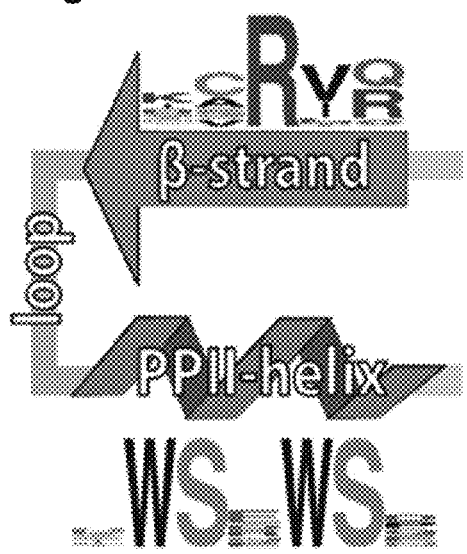
FIGS. 1A and 1B. Cation-π interaction networks stabilize "WSXWS motifs" in native proteins. (1A) Sequence logo (22) and cartoon representation of the conserved secondary structural elements observed in WSXWS motifs. (1B) Cartoon representation of the Fibronectin type III domain of IL3RB in gray (PDBid: 1EGJ) with the WSXWS motif highlighted in blue (β-strand), cyan (loop), and purple (PPII-helix). (inset) The cation-π interaction network found in the X-ray structure of IL3RB. The dotted yellow lines highlight the connectivity of the cation-π interaction network formed between arginine (blue) and tryptophan (purple) side chains.
Figure 1B:
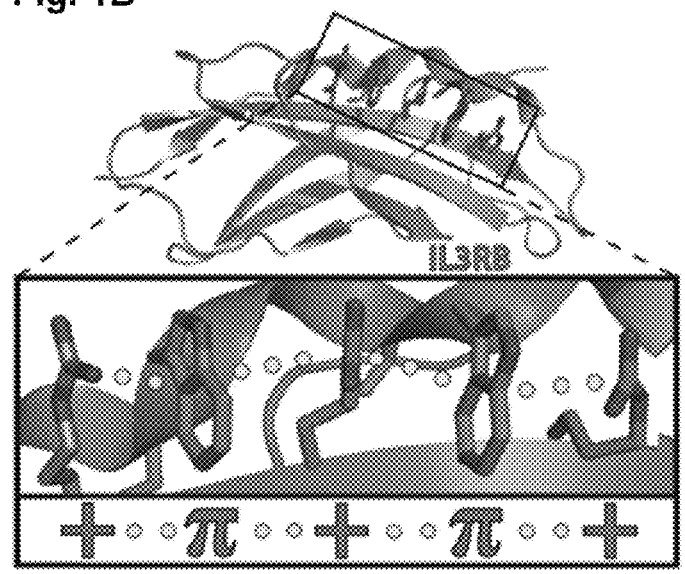
Figure 2:
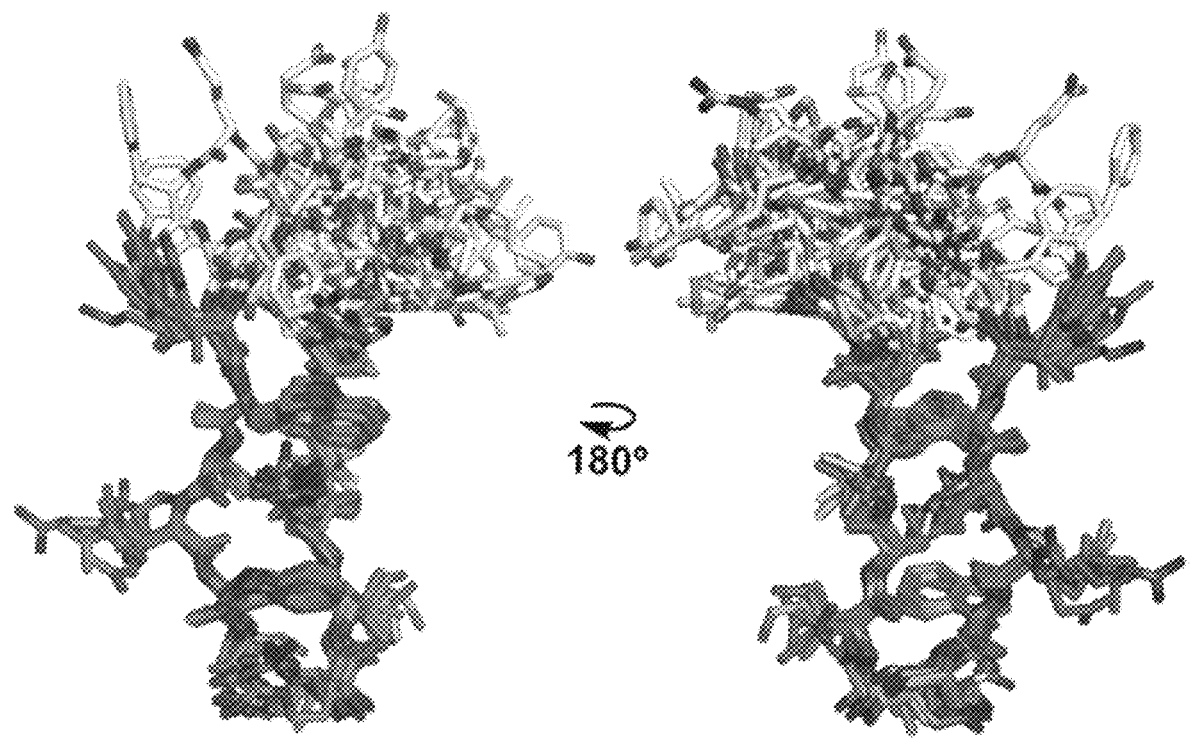
FIG. 2. Structural alignment of 15 X-ray structures of WSXWS motifs (23-37). β-strands, loops, and PPII-helical secondary structure elements can be seen in blue, gray, and purple respectively.

Networks of cation-π interactions are evident in X-ray crystal structures of numerous proteins. One example is the "WSXWS motif" found in fibronectin type III (Fn3) domain containing proteins (FIG. 1). The cation-π interactions in these motifs can be observed in X-ray structures stabilizing a relatively rare class of secondary structure, the left-handed poly proline type-II helix (PPII) (FIGS. 1, 2). In particular, an unusual PPII-helix devoid of proline residues has been observed in the sequences and structures of several Fn3 domains (FIGS. 1 and 2, Table 1). The present inventors sought to extract and replicate the β-strand:loop:PPII-helix topology observed in these motifs and determine whether this tertiary structure could exist in the absence of the parent Fn3 protein domain. Results presented herein detail the successful design of a 19-residue mini-protein that emulates the tertiary structure of WSXWS motifs including a core network of cation-π interactions.

TABLE 1

UniprotIDs and Multiple Sequence Alignment of WSXWS Motifs Found in X-ray Crystal Structures (23-37)

| Uniprot ID | Multiple Sequence Alignment |
|---|---|
| P40189 | RIRCMKEDGKG....YWSDWSE |
| P14784 | QVRVKPLQGEFT...TWSPWSQ |
| P31785 | RVTSRFNPLCGSAQ.HWSEWSH |
| P78552 | RIRVKTNKLCYEDDKLWSNWSQ |
| P40223 | QMRCIRSSLPG....FWSPWSP |
| P19235 | AVRARMAEPSFGG..FWSEWSE |
| Q99062 | QIRCIRWPLPG....HWSDWSP |
| P42702 | RIRCSTETFW.....KWSKWSN |
| P05710 | QTRCKPDHG......YWSRWSQ |
| Q14627 | VVRSKVNIYCSDDG.IWSEWSE |
| P08887 | QLRAQEEFGQG....EWSEWSP |
| Q01344 | QVRAAVSSMCREAG.LWSEWSQ |
| Q9HBE5 | QVRAGPMPGSSYQG.TWSEWSD |
| P48357 | QVRCKRLDGLG....YWSNWSN |
| P32927[a] | RVRVRTSRTGYNG..IWSEWSE |
| consensus | + + +            WS WS |

[a]The common name for P32927 is IL3RB.
Note:
Additional information about X-ray structures of WSXWS motifs including their PDB identifiers can be found in FIG. 7.

WSXWS Motifs in Natural Proteins.

WSXWS motifs are found in the structures of proteins comprising an Fn3 domain and include a β-strand:loop:PPII topology (FIG. 1) with a conserved "R . . . WSWS" primary sequence (Table 1). The structures feature a conserved arginine side chain intercalated between the two tryptophan residues (R . . . WSWS, FIG. 3A). Additionally, the hydroxyl groups of the conserved serine residues (R . . . WSWS) serve as hydrogen bond acceptors from an adjacent β-strand, as well as potential hydrogen bond donors to the i−1 carbonyl oxygen (FIG. 3B). The serine backbone amide HN groups also provide hydrogen bond donors to the adjacent β-strand. In some proteins, such as IL3RB (FIG. 1, Table 1), the WSXWS motif is stabilized by a core network of cation-π interactions involving three arginine residues on a β-strand, which interdigitate with two tryptophan residues of an adjacent PPII-helix. The WSXWS motifs have been the focus of extensive biological studies, as they are found in a wide array of extracellular receptors. These motifs are also subject to unique C-mannosylation of their conserved tryptophan residues (PDBid: 3TGX). In addition, a variety of genetic alterations within these sequences are associated with "X-linked severe combined immunodeficiency", (OMIMid: XSCID; a.k.a. "bubble boy syndrome") revealing the critical role played by the WSXWS motifs.

PPII-Helices in Miniature Proteins.

Proline-free PPII-helices are difficult to design. Unlike other secondary structure types, the PPII-helix does not feature a propagating hydrogen bonded network. With three residues per helical turn, the cofacial i and i+3 PPII positions are, on average, 8 Å apart (Cα→Cα), and are too distant to generate strong noncovalent interactions. Both the Trp-cage and the Avian Pancreatic Peptide (APP) miniproteins (3, 6) include a proline-rich PPII-helix packed against an α-helix generating an α-helix:loop:PPII topology. The structural rigidity engendered by multiple proline residues establishes an underlying foundation for interfacing α-helical elements. Thus, the rigidity of a PPII-helix has been demonstrated to augment the stability of proximal α-helical secondary structures. As described herein, the present inventors invert this relationship by stabilizing a proline-free PPII-helix through a set of stabilizing tertiary contacts with a neighboring peptide β-strand. Accordingly, the present results set forth a previously unexplored strategy for enforcing the left-handed PPII secondary structure type.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

As used herein, the term "immunomodulator" refers to an agent which is able to modulate an immune response. An example of such modulation is an enhancement of antibody production.

An "immunological response" to a composition or vaccine comprised of an antigen is the development in the host of a cellular- and/or antibody-mediated immune response to the composition or vaccine of interest. Usually, such a response consists of the subject producing antibodies, B cells, helper T cells, suppressor T cells, and/or cytotoxic T cells directed specifically to an antigen or antigens included in the composition or vaccine of interest. A polypeptide (or protein) is a linear chain of amino acids connected by peptide bonds. $NH_2$ refers to the free amino group present at one end, the amino terminus, of a polypeptide. COOH refers to the free carboxyl group present at the other end, the carboxy terminus of a polypeptide. The amino acid residues in a naturally-occurring polypeptide or protein are always in the "L" isomeric form. However, in a synthetic polypeptide, residues in the "D" isomeric form can be substituted for L-amino acid residues, as long as the desired functional property is retained by the polypeptide. Peptides with D-aminoacyl residues are likely to be less susceptible to proteolytic degradation. In keeping with standard polypeptide nomenclature, J. Biol. Chem., 243:3552-59 (1969), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of intracellular DNA replication; i.e., capable of replication under its own control.

A "vector" is a replicon, such as plasmid, phage or cosmid, to which another DNA segment may be attached so as to bring about the replication and expression of the attached segment.

A "DNA molecule" refers to the polymeric form of deoxyribonucleotides (adenine, guanine, thymine, or cytosine) either in its single stranded form, or as a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments, PCR products), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the RNA transcript (mRNA) by means of which gene products encoded in the DNA are expressed.

An "origin of replication" refers to a DNA sequence at which DNA synthesis is initiated.

A DNA "coding sequence" is a double-stranded DNA sequence which is transcribed into an mRNA which is translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA reverse transcribed from eukaryotic mRNA, genomic DNA sequences from eukaryotic (e.g., mammalian) DNA, and even synthetic DNA sequences. A transcription termination sequence will usually be located 3' to the coding sequence in both prokaryotes and eukaryotes. In eukaryotes there is usually a 3' polyadenylation signal.

Transcription and translation are controlled by regulatory DNA sequences such as promoters, enhancers, polyadenylation signals, terminators, and the like, that enable the synthesis of a protein from a genetic coding sequence in a cell.

A "promoter sequence" is a DNA regulatory region capable of binding RNA polymerase and initiating transcription of a downstream (3' direction) coding sequence. For purposes of defining the present invention, the promoter sequence is bounded at its 3' terminus by the transcription initiation site (conveniently defined by mapping with nuclease S1) and extends upstream (5' direction) to include the minimum number of nucleotides necessary for the initiation of transcription by RNA polymerase. Within the promoter sequence are highly conserved sequence motifs responsible for the binding of RNA polymerase. Eukaryotic promoters will often, but not always, contain conserved "TATA" and "CAT" motifs. Most prokaryotic promoters contain consensus "TATAAT" and "TTGACA" motifs located at 10 and 35 nucleotides upstream of (5' to) the transcription start site. Downstream of the transcription start site is a ribosome binding (Shine-Dalgarno) site, with the consensus sequence "AGGAGGA". This site, 7-14 nucleotides upstream of the translation start codon, enables binding of the ribosome for the initiation of translation.

RNA polymerase transcribes a coding sequence into mRNA, which is then translated into the protein encoded by the coding sequence. These processes are regulated by "expression control sequences", DNA sequences that control and regulates the transcription and translation of protein coding DNA sequences. A coding sequence is "under the control" of transcriptional and translational control sequences in a cell which determine the timing and level of expression of that coding sequence. The vast majority of prokaryotic and eukaryotic proteins destined for secretion or for incorporation into the cell envelope contain "signal peptide sequences" at the N-terminal end of the coding sequence. These sequences encode signal peptides that communicate to the host cell to direct the polypeptide to the cell surface or to be secreted into the medium, and the signal peptide is clipped off by an enzyme, signal peptidase, before the protein leaves the cell.

The term "oligonucleotide," as used herein is defined as a polymeric nucleic acid molecule usually comprised of 20 or more nucleotides, almost always DNA, and usually synthesized chemically. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid template, is induced, i.e., in the presence of nucleotides and a DNA polymerase and at a suitable temperature and pH. The primer is generally single-stranded and must be sufficiently long to hybridize stably with a template nucleic acid so as to prime the synthesis of the desired extension product in the presence of the polymerase. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides. The primers herein are selected to be "substantially" complementary to a particular target DNA sequence. This means that the primers must be sufficiently complementary to hybridize with their respective strands. Therefore, the primer sequence need not reflect the exact sequence of the template. For example, a non-complementary nucleotide sequence may be attached to either end of the primer, with the remainder of the primer sequence being complementary to the target strand. Alternatively, non-complementary bases or longer sequences can be interspersed into the primer, provided that the primer sequence has sufficient complementarity with the sequence of the target strand to hybridize therewith and thereby form the template for the synthesis of the extension product.

As used herein, the terms "restriction endonucleases" and "restriction enzymes" refer to bacterial enzymes, which cut double-stranded DNA at or near a specific nucleotide recognition sequence.

A cell has been "transformed" by exogenous or heterologous DNA when such DNA has been introduced inside the cell and has become a stable component of the cell's genome. The transforming DNA may or may not be integrated (covalently linked) into chromosomal DNA, the cell's major genophore. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

It should be appreciated that also within the scope of the present invention are DNA sequences encoding a protein having the same amino acid sequence as a given protein but a different DNA sequence. This is possible because up to 6 different three-letter codons are used to specify a particular amino acid. The second sequence is considered degenerate to the first. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |

-continued

| | |
|---|---|
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

Mutations can be made in a protein coding sequence, such that a particular codon is changed to a codon which codes for a different amino acid. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing either conservative changes which do not significantly alter the activity or binding characteristics of the resulting protein, or non-conservative changes which significantly alter the activity or binding characteristics of the resulting protein.

The following is one example of various groupings of amino acids:

Amino acids with nonpolar R groups—Alanine, Valine, Leucine, Isoleucine, Proline, Phenylalanine, Tryptophan, Methionine Amino acids with uncharged polar R groups—Glycine, Serine, Threonine, Cysteine, Tyrosine, Asparagine, Glutamine Amino acids with charged polar R groups (negatively charged at pH 6.0)—Aspartic acid, Glutamic acid Basic amino acids (positively charged at pH 6.0)—Lysine, Arginine, Histidine (at pH 6.0)

Another grouping may be those amino acids with phenyl groups: Phenylalanine, Tryptophan, Tyrosine Another grouping may be according to molecular weight (i.e., size of R groups):

| | |
|---|---|
| Glycine | 75 |
| Alanine | 89 |
| Serine | 105 |
| Proline | 115 |

| | |
|---|---|
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly conservative substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Amino acid substitutions may also be introduced to substitute an amino acid with a particularly preferable property. For example, a Cys may be introduced to provide a potential site for a disulfide bridge with another Cys. A His may be introduced as a particularly "catalytic" site (i.e., His can act as an acid or base and is the most common amino acid in enzymatic catalysis). Pro may be introduced because of its particularly planar structure, which induces angular turns in the protein's structure, thus disrupting alpha helices.

Amino acid substitutions may also be introduced to substitute an amino acid comprising a non-natural cationic side chain.

With respect to amino acid substitutions involving replacement with a proline, prolines bearing cationic substituents are also envisioned herein.

Two amino acid sequences are "substantially homologous" when at least about 70% of the amino acid residues (preferably at least about 80%, and most preferably at least about 90 or 95%) are identical, or represent conservative substitutions.

A "heterologous" region of a DNA construct is an identifiable segment of DNA within a larger DNA molecule that is not found in association with the larger molecule in nature. Thus, when the heterologous region contains a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein, whereas the insertion of a transposable element ("transposon"), a prophage, or an integrating pathogenicity island does give rise to a heterologous region.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An antigen is any substance that induces the formation of antibodies in a eukaryotic organism. An immunologically active segment of a protein antigen is known as an "epitope". An "antibody combining site" is that structural portion of an antibody molecule comprised of heavy and light chain variable and hypervariable regions that specifically binds antigen. The phrase "antibody molecule" in its various grammatical forms as used herein contemplates both an intact immunoglobulin molecule and an immunologically active portion of an immunoglobulin molecule.

The phrase "pharmaceutically acceptable" refers to molecular entities and compositions that are physiologically tolerable and do not typically produce an adverse allergic or similar untoward reaction, such as gastric upset, dizziness and the like, when administered to a human. As used herein, the term "operably linked" or "operatively linked" refers to a regulatory sequence capable of mediating the expression of a coding sequence, which is placed in a DNA molecule (e.g., an expression vector) in an appropriate position relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20$^{\circ}$C below the predicted or determined $T_m$ with washes of higher stringency, if desired.

Poly Proline Type-II Helices and Uses Thereof

Originally characterized in fibrillar proteins, the PPII helix is a structural class that has been identified in folded and unfolded proteins. PPII helices are known to function in a variety of signal transduction cascades and are involved in the assembly of protein complexes. It is also well established that PPII helices contribute to transcriptional regulation, cellular motility, self-assembly of protein complexes, protein elasticity, and bacterial and viral pathogenesis. See, for example, Adzhubei et al. (2013, J Mol Biol 425:2100-2132; the entire content of which is incorporated herein by reference). Indeed, PPII helices are recognized as playing a major role in protein-protein interactions and protein-nucleic acid interactions. PPII helices are frequently identified as components of binding sites and are recognized as binding sites for proline rich domains (PRDs), a class of domains that includes SH3 and WW domains. A list of functions attributed to PPII helices is presented in Table 1 of Adzhubei et al. (supra), which list underscores the myriad of binding interactions to which PPII helices contribute. As detailed therein, PPII helices serve as ligands for SH3 domains (e.g., SH3 domains of Src tyrosine kinases), WW, GYF, EVH1, UVE, and profilin domains.

Accordingly, a miniature protein scaffold described herein can be used to mimic a PPII helix that plays a role in a specific protein-protein or protein-nucleic acid interaction and thus provide an agent that could be used to compete with and thereby inhibit the specific interaction. A miniature protein scaffold described herein can, moreover, be engineered/modified to mimic with greater particularity a PPII helix that plays a role in a specific protein-protein or protein-nucleic acid interaction and thus provide an agent that could be used to compete with and thereby inhibit the specific interaction. Alternatively, a miniature protein scaffold described herein could be engineered/modified to promote a protein-protein or protein-nucleic acid interaction. A miniature protein scaffold described herein may also be engineered/modified to activate, inactivate, and/or target a protein comprising a PRD. See, for example, Hobert and Schepartz (2012, J Am Chem Soc 134:3976; the entire content of which is incorporated herein by reference).

In another embodiment, a miniature protein scaffold described herein could be modified to mimic a PPII helix that serves as part of or the entirety of an antigenic determinant of a protein recognized by the immune system. In such an embodiment, the modified miniature protein scaffold could be used as the antigenic component of a vaccine designed to elicit an immune reaction to the protein in question. In a particular embodiment, the protein could be expressed by pathogen (e.g., virus, bacteria, fungus, or parasite) against which it is desirable to promote a robust immune reaction. In certain embodiments thereof, the modified miniature protein scaffold would be administered in the context of a pharmaceutically acceptable composition, which may further comprise one or more adjuvants.

Adjuvants:

Vaccine adjuvants are useful for improving an immune response obtained with any particular antigen in a vaccine composition. Adjuvants are used to increase the amount of antibody and effector T cells produced and to reduce the quantity of antigen and the frequency of injection. Although some antigens are administered in vaccines without an adjuvant, there are many antigens that lack sufficient immunogenicity to stimulate a useful immune response in the absence of an effective adjuvant. Adjuvants also improve the immune response from "self-sufficient" antigens, in that the immune response obtained may be increased or the amount of antigen administered may be reduced. An adjuvant can serve as a tissue depot that slowly releases the antigen and also as a lymphoid system activator that non-specifically enhances the immune response (Hood et al., *Immunology, Second Ed.*, 1984, Benjamin/Cummings: Menlo Park, Calif., p. 384).

The standard adjuvant for use in laboratory animals is Freund's adjuvant. Freund's Complete adjuvant (FCA) is an emulsion containing mineral oil and killed mycobacteria in saline. Freund's incomplete adjuvant (FIA) omits the mycobacteria. Both FIA and FCA induce good humoral (antibody) immunity, and FCA additionally induces high levels of cell-mediated immunity. However, neither FCA nor FIA are acceptable for clinical use due to the side effects. In particular, mineral oil is known to cause granulomas and abscesses, and *Mycobacterium tuberculosis* is the agent responsible for tuberculosis.

Previously known and utilized adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (bacille Calmette-Guerin) and *Corynebacterium parvum*. Mineral salt adjuvants include but are not limited to: aluminum hydroxide, aluminum phosphate, calcium phosphate, zinc hydroxide and calcium hydroxide. Preferably, the adjuvant composition further comprises a lipid or fat emulsion comprising about 10% (by weight) vegetable oil and about 1-2% (by weight) phospholipids. Preferably, the adjuvant composition further optionally comprises an emulsion form having oily particles dispersed in a continuous aqueous phase, having an emulsion forming polyol in an amount of from about 0.2% (by weight) to about 49% (by weight), optionally a metabolizable oil in an emulsion-forming amount of up to 15% (by weight), and optionally a glycol ether-based surfactant in an emulsion-stabilizing amount of up to about 5% (by weight).

Many other substances that have been tested as adjuvants, including the lipid-A portion of gram negative bacterial endotoxin, and trehalose dimycolate of mycobacteria. The phospholipid lysolecithin exhibited adjuvant activity (Arnold et al., Eur. J Immunol. 9:363-366, 1979). Some synthetic surfactants exhibited adjuvant activity, including dimethyldioctadecyl ammonium bromide (DDA) and certain linear polyoxypropylenepolyoxyethylene (POP-POE) block polymers (Snippe et al., Int. Arch. Allergy Appl. Immunol. 65:390-398, 1981; and Hunter et al., J. Immunol. 127:1244-1250, 1981).

With respect to humans, the use of alum as an adjuvant is envisioned. For cattle, CpG oligodeoxynucleotide or saponin are envisioned as suitable adjuvants.

According to the invention, miniature protein scaffolds and immunogenic compositions thereof may be administered subcutaneously or intramuscularly. Quantities of the miniature protein scaffolds and immunogenic compositions thereof to be used for immunization will be determined experimentally.

As used herein, "pg" means picogram, "ng" means nanogram, "ug" or "µg" mean microgram, "mg" means milligram, "ul" or "µl" mean microliter, "ml" means milliliter, "l" means liter.

A general method for site-specific incorporation of unnatural amino acids into proteins is described in Christopher J. Noren, Spencer J. Anthony-Cahill, Michael C. Griffith, Peter G. Schultz, *Science*, 244:182-188 (April 1989). This method may be used to create analogs with unnatural amino acids.

The invention may be better understood by reference to the following non-limiting examples, which are provided as exemplary of the invention. The following examples are presented in order to more fully illustrate the preferred embodiments of the invention and should in no way be construed, however, as limiting the broad scope of the invention.

Example 1

Methods and Materials

Peptide Synthesis.

All peptides were synthesized using standard FMOC solid-phase chemistry on 2-chlorotrityl (2-ClTrt) resin (Anaspec, Fremont, Calif.) using PyBop (benzotriazol-1-yl-oxytripyrrolidinophosphonium hexafluorophosphate) activating agent (Anaspec, Fremont, Calif.). All peptides were precipitated out of cold ether and purified by reverse-phase HPLC using preparative chromatography and eluted with $H_2O$-Acetonitrile (ACN) gradients in 0.1% trifluoroacetic acid (TFA). After purification, all proteins were lyophilized three times in 1:1:1 (v:v:v) $H_2O$:ACN:Acetic Acid to remove TFA salts and transferred into buffer with pH adjustment after protein addition. Protein stock solutions at 2.0 mM concentrations were stored at −20° C. All peptides were characterized by mass analysis using MALDITOF MS or ESI MS; sequence and purity were evaluated by HPLC and NMR spectroscopy analysis. Disulfide-bridged peptides were synthesized, purified, and characterized in an analogous way but instead were cleaved from 2-ClTrt resin using a 90:5:3:2 (v:v:v:v) mixture of TFA:thioanisole:ethanedithiol:anisole.

Circular Dichroism (CD).

CD spectra were collected using an Aviv (Lakewood, N.J.) stopped flow CD Spectropolarimeter Model 202SF. The far-UV (190-260 nm) CD spectra were obtained using a 1 mm path length cell and in 10 mM PBS buffer at a pH of 7.5 at 100 μM protein concentrations. The near-UV (245-320 nm) CD spectra were obtained using a 1 cm path length cell and in 10 mM PBS buffer at a pH of 7.5 at 50 μM concentrations. The consensus CD spectra were established as the Gaussian weighted average of 40 scans with evaluation of ellipticity every 0.5 nm, each having an averaging time of 0.5 s. Proper "blank" spectra were subtracted from all multiple wavelength and single-wavelength spectra and thermal melts utilizing the equation $(\Theta\text{sample}-\Theta\text{"blank"})/(L\cdot c\cdot n)$ where L is the path length, c is the protein concentration, and n is the number of amino acids in the sequence. CD spectra are presented unsmoothed. Concentrations of protein stock solutions for conversion of millidegrees to mean residue ellipticity (MRE) were determined by UV absorbance at 280 nm using the standard extinction coefficients for the tryptophan (5690 M-1 cm-1), tyrosine (1280M-1 cm-1), and disulfide-bridged cysteine (125M-1 cm-1) chromophores in 6 M GnCl. Thermal melts were conducted using a 1° C./min temperature gradient, a 1 min equilibration time at each temperature step, and an average of 20 single wavelength measurements. Spectra for GnCl concentrations that spanned the folded to unfolded transition are presented in FIG. 4B and their MRE values at 280 nm were converted to $\Delta G°$ at 25° C. using the equation $\Delta G°=-RT \ln Q$ where $Q=\chi/1-\chi$ and $\chi$ is the fraction of folded protein at the given concentration of GnCl. $\Delta G°$ values were plotted versus the concentration of GnCl and least-squares fit to a linear equation in order to extrapolate the y-intercept value corresponding to the $\Delta G°$ in native buffer at 25° C.

NMR Spectroscopy.

NMR spectra were collected using a Bruker (Billerica, Mass.) AVANCE 111-600 NMR spectrometer equipped with a TCI CryoProbe. All samples were prepared in $H_2O$ and $D_2O$ that had been purged of dissolved $O_2$ gas using the freeze-pump-thaw method. 1D and 2D $^1H$ NMR were collected at protein concentrations of 1.8 mM in 90% $H_2O$:10% $D_2O$ solutions at pH 3.8 (uncorrected). For determination of $^3J_{HN-H\alpha}$ values, 1D $^1H$ NMR spectra were obtained with 32 k complex data points. Total correlated spectroscopy (TOCSY) spectra were collected utilizing a mixing time of 120 ms using Bruker's mlevesgpph pulse sequence. 2D $^1H$-$^1H$ nuclear Overhauser effect spectroscopy (NOESY) spectra were collected utilizing a 250 ms mixing time using Bruker's noesyesgpph pulse sequence. All chemical shifts are reported relative to a 4,4-dimethyl-4-silapentane-1-sulfonic acid (DSS) internal standard.

NMR Structure Ensemble.

NMR assignment and volume calculations were performed using the Sparky NMR package. Using the Rosetta Molecular Modeling package (39), 50 000 structures were initialized with φ values to one of the two values dictated by an empirically derived Karplus equation $(6.51\cdot\cos 2(\varphi-60)-1.76\cdot\cos(\varphi-60)+1.635)$ (40) for 3JHN-Hα values >6.4 Hz (Table S4). Glycine residues were initialized and randomized into the full range of φ/ψ values. Distance constraints were calculated using the tryptophan indole reference cross-peak volume from W15Hη2→W15Hζ3 as this has a known reference distance of 2.46 Å. Other indole ring proton cross-peak volumes with similar distances were also found close to this reference volume (Vref). The distance from proton i to j was calculated using the equation $d_{i,j}=2.46\cdot(Vref/Vi,j)(⅙)$. Upon the basis of these calculated distances, NOEs were characterized as strong (1.8-2.5 Å), medium (1.8-3.3 Å), or weak (1.8-5.0 Å). Structures were minimized simultaneously with respect to energy and distance constraints (with "soft" 2.5 Å tolerances) using an Armijo type line-search algorithm within a Monte Carlo Metropolis acceptance criterion algorithm. Randomized backbone φ moves were limited to values within the bounds dictated by the Karplus equation ±30°. The 25 lowest energy sequences were found to obey all distance constraints within tolerances and were aligned using their Cα backbone atoms. The structure was further supported by conducting identical calculations using the Xplor-NIH software package (41, 42). Using a standard Xplor-NIH simulated annealing minimization of 10 000 structures, sequences were found to converge to the same backbone structure determined by the Rosetta calculations (FIG. 13).

TABLE S4

φ values obtained from an empirically derived Karplus equation (40).

| Residue | $^3J_{HN-H\alpha}$ (Hz) | $\varphi_1$ (degrees) | $\varphi_2$ (degrees) |
|---|---|---|---|
| R1 | | | |
| V2 | 7.3 | −155.6 | −84.2 |
| R3 | 7.1 | −157.0 | −91.8 |
| V4 | 8.3 | −147.2 | −91.7 |
| R5 | 7.2 | −156.2 | −82.3 |
| T6 | 8.4 | −145.8 | −94.0 |
| S7 | 7.1 | −156.7 | −83.0 |
| R8 | 7.3 | −155.6 | −82.7 |
| p9 | | | |
| G10 | 6.3 | | |
| Y11 | 7.0 | −158.5 | −82.4 |
| N12 | 7.5 | −154.4 | −85.5 |
| G13 | 5.9 | | |
| T14 | 7.7 | −153.0 | −87.9 |
| W15 | 7.4 | −157.0 | −85.4 |
| S16 | 6.8 | −160.4 | −80.3 |
| E17 | 6.4 | −164.1 | −77.3 |
| W18 | 7.8 | −150.8 | −88.7 |
| S19 | 7.5 | −153.7 | −86.1 |

Sedimentation Equilibrium.

Sedimentation equilibrium measurements were carried out on a Beckman (Brea, Calif.) XL-A analytical ultracentrifuge equipped with absorption optics and an An-60 Ti rotor. Analysis was conducted at rotor speeds of 45,000 and 48,000 rpm at 4° C. Data were acquired at two wavelengths per rotor speed setting and processed globally for the best fit to a single-species model of absorbance versus radial distance. Solvent density and protein partial specific volume were calculated according to solvent and protein composition, respectively.

Fluorescence Spectroscopy.

Fluorescence spectra were obtained using a 1 cm by 2 mm path length cell (excitation path length versus emission path length) in 10 mM PBS buffer at a pH of 7.5 and 50 μM peptide concentrations. The fluorometer was configured with a calibrated Peltier temperature controller.

Miscellaneous.

Least-squares fitting and graphical plotting was performed using the Scientific Python (scipy) scipy.optimize.curve_fit and matplotlib libraries. All 3-dimensional-cartoon protein graphics were created using the Schrodinger (New York, N.Y.) PyMOL software package.

TABLE S6

Arginine rotamers for each position in the WSXWS motif along with the number of observations of each rotamer grouping or bin. Analysis of these rotamers can be seen in FIGS. 3A and 3B.

| R1 | | R3 | | R5 | |
|---|---|---|---|---|---|
| Rotamer bin | Number of observations | Rotamer bin | Number of observations | Rotamer bin | Number of observations |
| '1 1 1 2' | 1 | '2 2 1 2' | 1 | '1 1 1 1' | 1 |
| '1 2 2 2' | 2 | '1 2 2 2' | 9 | '2 3 3 1' | 1 |
| '2 1 2 3' | 1 | '1 2 3 2' | 3 | '2 2 2 2' | 1 |
| '3 2 3 2' | 2 | '2 3 2 2' | 1 | | |
| | | '2 2 2 2' | 2 | | |

TABLE S7

Chemical shifts for the TrpPlexus sequence at 4C.
All chemical shifts are referenced to a DSS standard.
TrpPlexus 4C pH 3.8
RVRVRTSRpGYNGTWSEWS

| # | Res. | HN | Hα | Hβ | Hγ | Hδ | Other: |
|---|---|---|---|---|---|---|---|
| 1 | Arg | | 4.098 | 1.850 | 1.546 | 2.987 | Hε: 7.102 |
| 2 | Val | 8.860 | 4.292 | 1.998 | 0.898 | | |
| 3 | Arg | 8.662 | 4.351 | 1.533 | 1.329, 1.246 | 2.841 | Hε: 6.957 |
| 4 | Val | 8.580 | 4.301 | 1.992 | 0.867 | | |
| 5 | Arg | 8.631 | 4.394 | 1.532 | 1.346, 1.184 | 2.734, 2.581 | Hε: 6.957 |
| 6 | Thr | 8.342 | 4.431 | 4.157 | 1.144 | | |
| 7 | Ser | 8.470 | 4.580 | 3.717 | | | |
| 8 | Arg | 8.575 | 4.616 | 1.669 | 1.483 | 2.897, 2.932 | Hε: 7.085 |
| 9 | D-Pro | | 4.340 | 2.217 | 1.933, 1.861 | 3.686, 3.560 | |
| 10 | Gly | 8.334 | 3.777 | | | | |
| 11 | Tyr | 8.119 | 4.521 | 2.98 | | 7.074 | Hε: 6.759 |
| 12 | Asn | 8.617 | 4.718 | 2.680, 2.630 | | 7.629, 6.956 | |
| 13 | Gly | 7.780 | 3.875, 3.774 | | | | |
| 14 | Thr | 8.108 | 4.346 | 4.115 | 1.115 | | |
| 15 | Trp | 8.416 | 4.671 | 3.192, 3.089 | | 7.136 | Hε1: 10.10, Hζ2: 7.363, Hη2: 7.105, Hζ3: 6.960, Hε3: 7.365 |
| 16 | Ser | 8.240 | 4.355 | 3.718, 3.615 | | | |
| 17 | Glu | 8.223 | 4.169 | 1.849, 1.735 | 2.092, 1.997 | | |
| 18 | Trp | 8.158 | 4.806 | 3.254, 3.084 | | 7.180 | Hε1: 10.09, Hζ2: 7.386, Hη2: 7.123, Hζ3: 7.028, Hε3: 7.445 |
| 19 | Ser | 8.108 | 4.352 | 3.789 | | | |

TABLE S8

Chemical shifts for the cyclic TrpPlexus sequence at 4C.
All chemical shifts are referenced to a DSS standard.
Cyclic TrpPlexus 4C pH 3.8
RCRVRTSRpGYNGTWSEWC (oxidized), disulfide C2→C19

| # | Res. | HN | Hα | Hβ | Hγ | Hδ | Other: |
|---|---|---|---|---|---|---|---|
| 1 | Arg | | 4.074 | 1.836 | 1.530 | 3.004 | Hε: 7.083 |
| 2 | Cys | 8.977 | 4.593 | 2.851 | | | |
| 3 | Arg | 8.707 | 4.346 | 1.635, 1.558 | 1.379, 1.320 | 2.818 | Hε: 6.894 |
| 4 | Val | 8.453 | 4.211 | 1.96 | 0.8484 | | |
| 5 | Arg | 8.628 | 4.315 | 1.577 | 1.402, 1.266 | 2.880, 2.702 | Hε: 6.967 |
| 6 | Thr | 8.371 | 4.386 | 4.148 | 1.119 | | |
| 7 | Ser | 8.404 | 4.537 | 3.719 | | | |
| 8 | Arg | 8.528 | 4.593 | 1.673 | 1.526, 1.446 | 2.924 | Hε: 7.066 |
| 9 | D-Pro | | 4.313 | 2.193 | 1.906, 1.821 | 3.664, 3.543 | |
| 10 | Gly | 8.392 | 3.773 | | | | |
| 11 | Tyr | 8.081 | 4.494 | 2.944 | | 7.032 | Hε: 6.729 |
| 12 | Asn | 8.556 | 4.671 | 2.664, 2.603 | | 7.586, 6.916 | |
| 13 | Gly | 7.746 | 3.840, 3.761 | | | | |
| 14 | Thr | 8.379 | 4.31 | 4.109 | 1.081 | | |
| 15 | Trp | 8.382 | 4.612 | 3.189, 3.107 | | 7.125 | Hε1: 10.07, Hζ2: 7.380, Hη2: 7.089, Hζ3: 6.961, Hε3: 7.376 |
| 16 | Ser | 8.193 | 4.303 | 3.697, 3.564 | | | |
| 17 | Glu | 8.214 | 4.14 | 1.786, 1.718 | 2.111, 2.035 | | |
| 18 | Trp | 8.184 | 4.757 | 3.227, 3.087 | | 7.153 | Hε1: 10.09, Hζ2: 7.357, Hη2: 7.111, Hζ3: 7.012, Hε3: 7.456 |
| 19 | Cys | 8.097 | 4.299 | 2.791 | | | |

TABLE S9

Table of amide temperature coefficients ($\Delta\sigma_{HN}/\Delta T$ (ppb/K)) observed for TrpPlexus plotted in a bar graph in FIG. S4A.

| # | Res. | $\Delta\sigma_{HN}/\Delta T$ (ppb/K) |
|---|------|---------|
| 1 | Arg | — |
| 2 | Val | 13.32 |
| 3 | Arg | 7.00 |
| 4 | Val | 9.22 |
| 5 | Arg | 6.95 |
| 6 | Thr | 7.13 |
| 7 | Ser | 6.21 |
| 8 | Arg | 6.95 |
| 9 | D-Pro | — |
| 10 | Gly | 6.73 |
| 11 | Tyr | 5.85 |
| 12 | Asn | 6.65 |
| 13 | Gly | 2.47 |
| 14 | Thr | 5.87 |
| 15 | Trp | 7.12 |
| 16 | Ser | 6.43 |
| 17 | Glu | 6.67 |
| 18 | Trp | 5.35 |
| 19 | Ser | 5.70 |

TABLE S10

Table of chemical shifts and chemical shift deviations at 25C from 'random coil' values for TrpPlexus seen plotted in FIG. 5C (black bars). An asterisk (*) denotes utilization of random coil values specifically for residues followed by proline. Hα CSDs, or Hα chemical shift deviations are calculated as (observed Hα δ) − ('random coil' Hα δ).

| # | Res. | Hα δ (ppm) | 'random coil' δ (ppm) | Hα CSD (ppm) |
|---|------|------------|------------------------|--------------|
| 1 | Arg | 4.143 | 4.34 | −0.197 |
| 2 | Val | 4.183 | 4.12 | 0.063 |
| 3 | Arg | 4.380 | 4.34 | 0.040 |
| 4 | Val | 4.201 | 4.12 | 0.081 |
| 5 | Arg | 4.385 | 4.34 | 0.045 |
| 6 | Thr | 4.429 | 4.35 | 0.079 |
| 7 | Ser | 4.455 | 4.47 | 0.065 |
| 8 | Arg | 4.633 | 4.65* | −0.017 |
| 9 | D-Pro | 4.360 | 4.42 | −0.060 |
| 10 | Gly | 3.837 | 3.96 | −0.123 |
| 11 | Tyr | 4.450 | 4.55 | −0.010 |
| 12 | Asn | 4.704 | 4.74 | −0.036 |
| 13 | Gly | 3.878 | 3.96 | −0.082 |
| 14 | Thr | 4.336 | 4.35 | −0.014 |
| 15 | Trp | 4.655 | 4.66 | −0.005 |
| 16 | Ser | 4.304 | 4.47 | −0.166 |
| 17 | Glu | 4.149 | 4.35 | −0.201 |
| 18 | Trp | 4.794 | 4.66 | 0.134 |
| 19 | Ser | 4.260 | 4.47 | −0.210 |

TABLE S11

Table of chemical shifts and chemical shift deviations at 25C from 'random coil' values for cyclic TrpPlexus structure seen plotted in FIG. 5C (green bars). An asterisk (*) denotes utilization of random coil values specifically for residues followed by proline. Hα CSDs, or Hα chemical shift deviations are calculated as (observed Hα δ) − ('random coil' Hα δ).

| # | Res. | Hα δ (ppm) | 'random coil' δ (ppm) | Hα CSD (ppm) |
|---|------|------------|------------------------|--------------|
| 1 | Arg | 4.084 | 4.34 | −0.256 |
| 2 | Cys (Oxidized) | 4.566 | 4.71 | −0.144 |
| 3 | Arg | 4.353 | 4.34 | 0.013 |
| 4 | Val | 4.184 | 4.12 | 0.064 |
| 5 | Arg | 4.347 | 4.34 | 0.007 |
| 6 | Thr | 4.410 | 4.35 | 0.060 |
| 7 | Ser | 4.535 | 4.47 | 0.065 |
| 8 | Arg | 4.616 | 4.65* | −0.034 |
| 9 | D-Pro | 4.344 | 4.42 | −0.076 |
| 10 | Gly | 3.815 | 3.96 | −0.145 |
| 11 | Tyr | 4.516 | 4.55 | −0.034 |
| 12 | Asn | 4.673 | 4.74 | −0.067 |
| 13 | Gly | 3.852 | 3.96 | −0.180 |
| 14 | Thr | 4.316 | 4.35 | −0.034 |
| 15 | Trp | 4.635 | 4.66 | −0.025 |
| 16 | Ser | 4.316 | 4.47 | −0.154 |
| 17 | Glu | 4.178 | 4.35 | −0.172 |
| 18 | Trp | 4.786 | 4.66 | 0.126 |
| 19 | Cys (Oxidized) | 4.316 | 4.71 | −0.394 |

Results and Discussion

Design and Characterization of a Mini-Protein Stabilized by a Cation-π Network.

The native sequence on which to initiate the mini-protein design was chosen based on two primary criteria. First, the present inventors sought a sequence containing a loop featuring a β-hairpin, which could be nucleated using a D-Pro-Gly motif (2, 7). Most of the loop regions observed in WSXWS motifs are lacking in canonical forms of secondary structure that could be enforced with rational peptide design (FIG. 2). Second, the present inventors wanted a sequence containing three arginine residues on the β-strand portion of the fold composing the cation-π interaction network. The only sequence meeting these two criteria was that of the WSXWS motif found in IL3RB (UniprotID: P32927). Thus, the investigation described herein began by synthesizing a modified 19-residue sequence from the WSXWS motif of IL3RB. The design included two modifications from the native sequence: D-Pro was incorporated at position 9 to promote a β-hairpin, and an Ile→Thr mutation was introduced at position 14 to enhance solubility. The resulting sequence, "RVRVRTSRpGYNGTWSEWS" is denoted as "TrpPlexus": a portmanteau of "tryptophan" and "plexus", signifying the network arrangement of stabilizing interactions (FIGS. 4 and 5) (43). TrpPlexus was found to be monomeric at a concentration of 1.8 mM at 4° C. by sedimentation equilibrium analysis (FIG. 4D) (44). The apparent molecular mass was within 10% of that calculated for an ideal monomer, with no systematic deviation of the residuals. The fluorescence emission spectrum (FIG. 4E) for TrpPlexus was observed to have two major emission wavelengths of similar intensities, one at 336 and 345 nm. A two-wavelength emission intensity plot is provided (FIG. 4E inset) as a proxy for the change in emission spectra shape as a function of temperature. A linear relationship between the intensities of the two emission maxima wavelengths was observed and the spectra were found to be completely reversible.

Figure 4A:
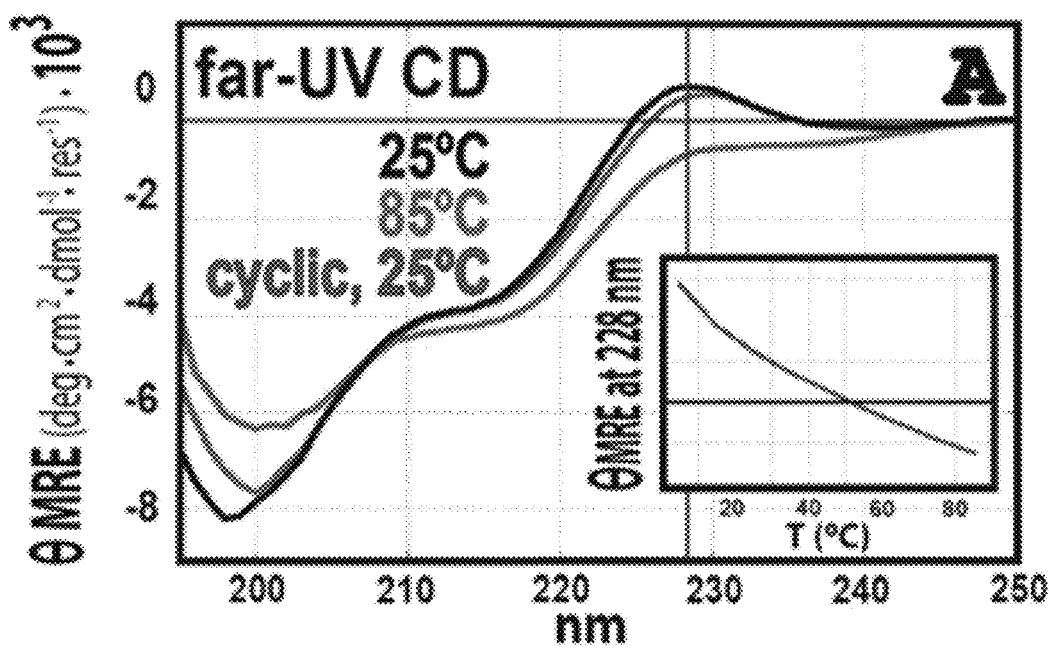
FIGS. 4A-4E. Spectroscopic evaluation of the TrpPlexus mini-protein. (4A) Far-UV Circular Dichroism spectra (50 μM protein, 1 cm path length, 10 mM PBS buffer pH 7.5) in units of mean residue ellipticity (MRE). Inset shows the relationship of the positive lobe of ellipticity at 228 nm as a function of temperature. (4B) Near-UV CD spectra (100 μM protein, 1 mm path length, 10 mM PBS buffer pH 7.5). (4C) GnCl titrations (50 μM protein, 1 cm path length). (inset) MRE values converted to fraction folded at a given concentration of GnCl from a least-squares fit to a sigmoidal function. (4D) Sedimentation equilibrium analysis. (4E) Temperature dependent fluorescence spectra (excitation 280 nm) in Arbitrary Units (A.U.). Inset provides dual wavelength fluorescence intensity plot (336 nm vs 345 nm).
Figure 4B:
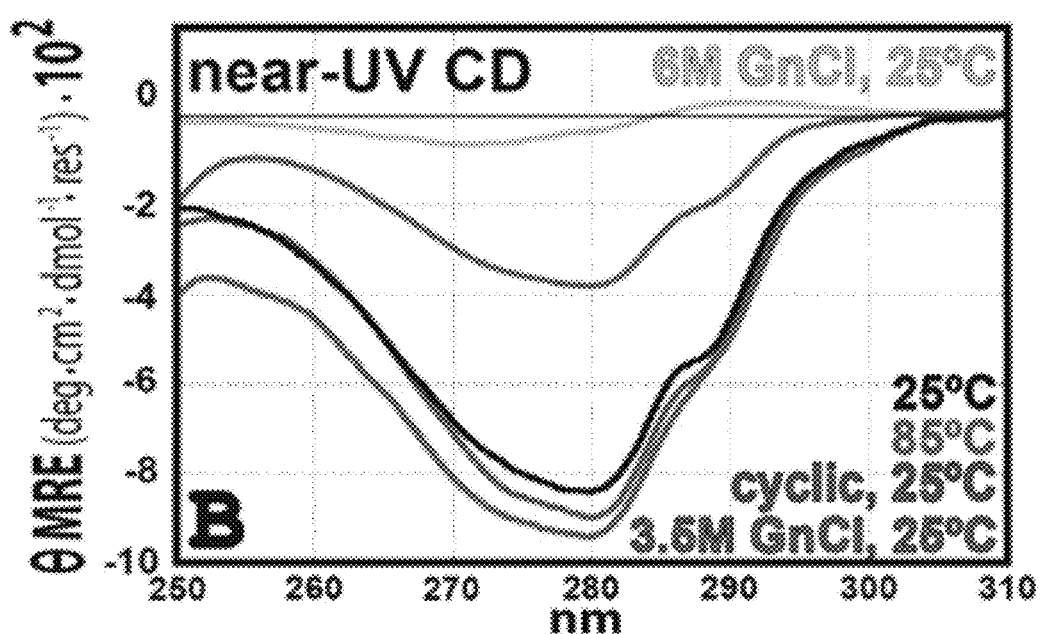
Figure 4C:
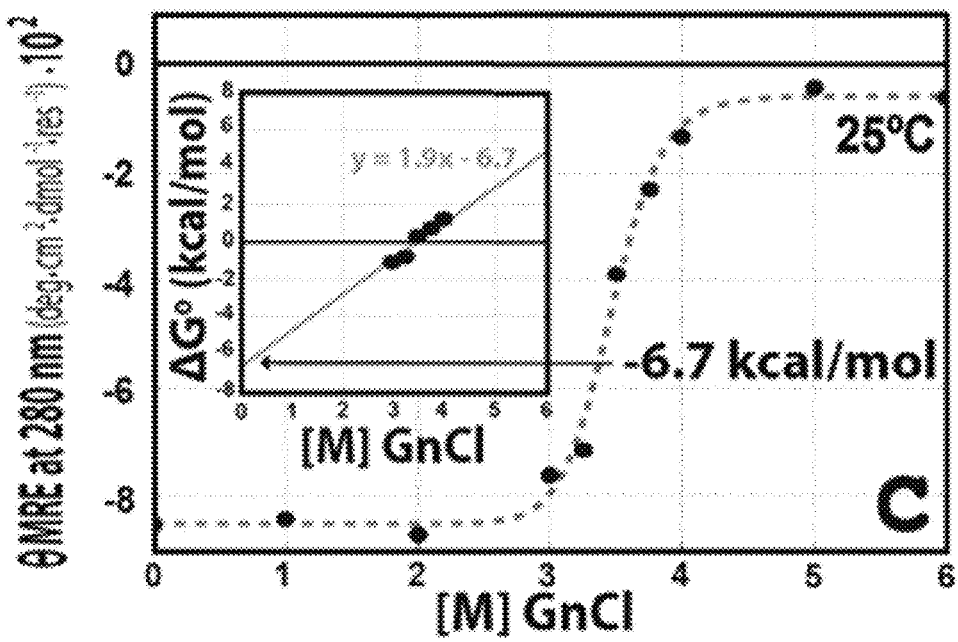
Figure 4D:
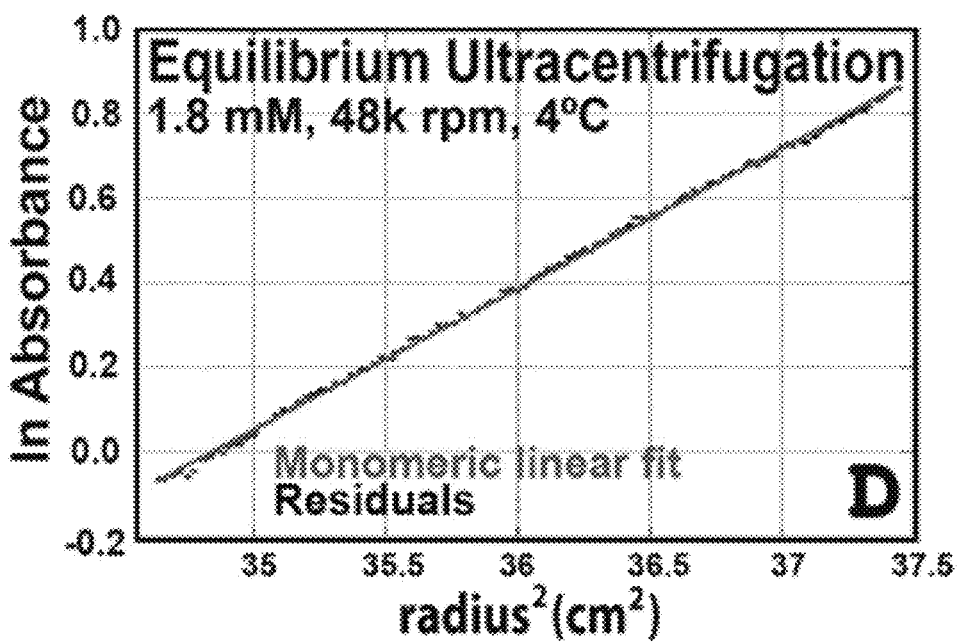
Figure 4E:
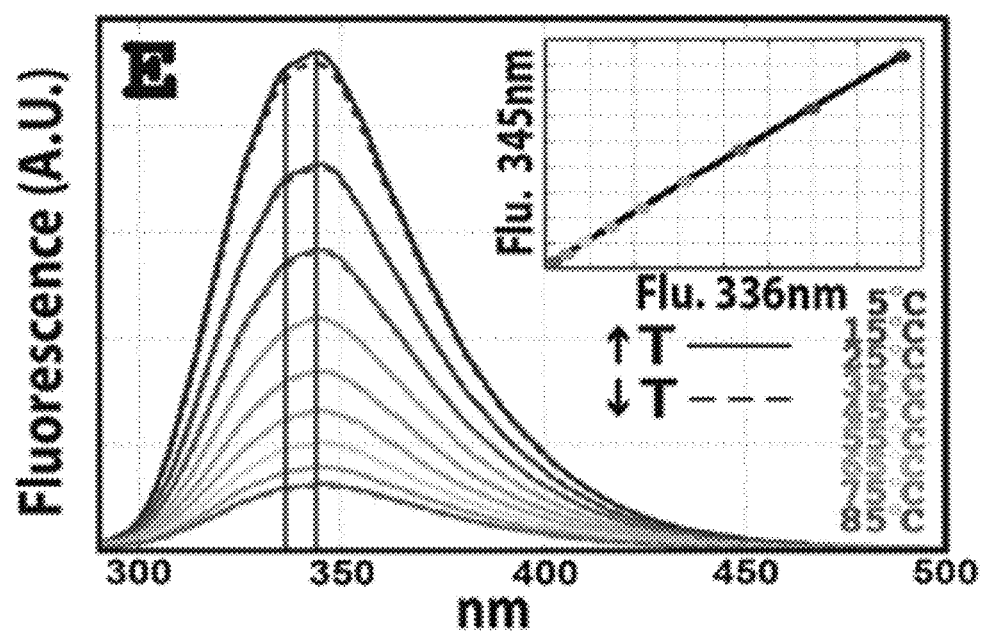

Secondary and tertiary structure content of the miniprotein was initially evaluated using circular dichroism (CD) spectroscopy (FIG. 4A,B). In the near-UV (260-320 nm) CD spectrum, ellipticity can arise from indole and phenol absorbance bands when tryptophan or tyrosine side chains are present in an asymmetric environment. Strong CD signals in this region are exclusively observed for sequences containing significant tertiary structure (45). Consequently, the near-UV CD signal is a stringent metric for the presence of tertiary structure. The strong near-UV CD signal for TrpPlexus was found to slightly increase in strength at elevated temperatures, indicating thermostability (FIG. 4B, see discussion presented herein). Conversely, the near-UV CD signal was observed to decrease in strength upon addition of the chaotropic agent guanidinium chloride (GnCl). The near-UV signal demonstrated two-state sigmoidal characteristics as a function of GnCl concentration. The variable GnCl concentration near-UV CD data correlate to a $\Delta G°$ for folding of approximately $-6.7$ kcal/mol in standard aqueous conditions at 25° C. (FIG. 4C). The far-UV (180-260 nm) CD spectrum includes features indicating the presence of a PPII-helix, such as a lobe of positive ellipticity at 228 nm (46-48) that can be attributed to the n→π* transition of amide groups present in a PPII-helix, as well as minor contributions from aromatic side chains (49) (FIG. 4A). The far-UV CD spectra also display similar temperature-dependent behavior observed in the spectra of other PPII-helical peptides (50).

In order to obtain an atomic-resolution solution structure, nuclear magnetic resonance (NMR) experiments were carried out on TrpPlexus (FIG. 5). Proton chemical shifts were assigned in the standard manner using $^1$H-$^1$H TOCSY experiments. Structural restraints to determine the three-dimensional structure were established using 2D $^1$H-$^1$H NOESY experiments. The assigned NOE cross-peaks were indicative of interdigitation of arginine and tryptophan residues and therefore complemented the near-UV CD data showing the presence of a highly ordered tertiary structure (FIG. 4B). Using a set of unambiguous distance constraints from the NOE spectrum including 12 long-range restraints (Tables S1-S3), the three-dimensional solution structure of TrpPlexus was determined that depicts a cation-π stabilized tertiary structure including a β-strand and a left-handed PPII-helix. The NMR ensemble structure is remarkably similar to the secondary and tertiary structure observed in the template WSXWS motif from the Fn3 domain of IL3RB with only minor differences. These small differences include alternate rotamers in the R8 and Y11 residues forming a more compact structure (FIG. 5A), and small deviations of the backbone dihedral angles for the ensemble typically within 30° of the angles observed in the X-ray structure of IL3RB. The ω dihedral angle of D-Pro9 was determined to be in a predominantly trans amide conformation as evidenced by strong R8Hα→p9Hδ NOEcross-peaks. Additionally, the presence of NOEs from G10HN→p9Hδ supports the presence of a type I' β-hairpin. In addition, the neighboring Asn-Gly (N12-G13) motif (1, 7, 9) serves to terminate the nascent β-strand, allowing for a transition to a left-handed PPII-helix. The patterning and relative intensities of the inter-residue and sequential NOE cross-peaks from both tryptophan indole groups match those expected for a PPII-helix displaying the most probable tryptophan rotamer (38, 51).

TABLE S1

List of the 12 unambiguous long-range distance constraints used in the generation of the NMR ensemble. Sequence distance (Seq. dist.) is the number of residues between the two highlighted in the linear sequence. The average ensemble distance (Avg. ensemble dist.) is the average distance each set of atoms is in the NMR ensemble structure.

| NOE cross-peaks | NOE strength | Seq. dist. | Avg. ensemble dist. (Å) |
|---|---|---|---|
| G13NH-Y11ε | medium | 2 | 3.42 |
| G13NH-Y11δ | medium | 2 | 2.26 |
| R1β-W18ε3 | medium | 17 | 2.48 |
| G13α-Y11δ | medium | 2 | 2.42 |
| S7β-N12α | weak | 5 | 3.21 |
| G13α-Y11δ | weak | 2 | 3.02 |
| G13NH-S7α | weak | 6 | 3.10 |
| T6γ-Y11δ | weak | 5 | 4.02 |
| S19NH-V2NH | weak | 17 | 2.29 |
| S7α-N12δ | weak | 5 | 5.10 |
| S19β-V2γ | weak | 17 | 4.57 |
| R8η-T6γ | weak | 2 | 3.90 |

TABLE S2

List of the 24 ambiguous long-range distance constraints used in the generation of the NMR ensemble.

| NOE cross-peaks | NOE strength | Seq. dist. | Avg. ensemble dist. (Å) |
|---|---|---|---|
| R3γ-W18η2 | medium | 15 | 3.82 |
| R1γ-W18ε3 | medium | 17 | 3.72 |
| R3β-W15ε3 | medium | 12 | 2.50 |
| R5δ-W15ε1 | medium | 10 | 3.39 |
| T6γ-R8ε | medium | 2 | 4.18 |
| V4α-W15ζ3 | medium | 11 | 3.08 |
| R5γ1-W15ζ2 | weak | 10 | 3.60 |
| W15ε3-R5α | weak | 10 | 4.20 |
| V4NH-W15ε3 | weak | 11 | 3.54 |
| W18ζ3-V2α | weak | 16 | 2.79 |
| R3δ-W18η2 | weak | 15 | 4.31 |
| R5γ2-W15ζ2 | weak | 10 | 4.39 |
| R5γ-W15δ1 | weak | 10 | 3.89 |
| S16β-V4γ | weak | 12 | 4.66 |
| W18ε3-R3α | weak | 15 | 4.56 |
| Y11NH-R8NH | weak | 3 | 2.95 |
| R8NH-Y11δ | weak | 3 | 4.88 |
| R5γ2-W15α | weak | 10 | 3.33 |
| T6γ-R8δ | weak | 2 | 3.60 |
| R3γ-W18ζ3 | weak | 15 | 3.24 |
| R3δ-W15β | weak | 12 | 3.77 |
| W18α-R3α | weak | 15 | 3.33 |
| V4β-S16β | weak | 12 | 3.31 |

TABLE S3

List of the 40 sequential and intra-residue distance constraints used in the generation of the NMR ensemble.

| NOE cross-peaks | NOE strength |
|---|---|
| W15NH-W15Hδ1 | strong |
| W18NH-W18Hδ1 | strong |
| G13NH-N12α | strong |
| R5NH-V4γ | strong |
| G10NH-Y11NH | strong |
| R5NH-V4α | strong |
| V4NH-R3α | strong |
| R3NH-V2α | strong |
| V2NH-R1α | strong |
| R8NH-S7α | strong |
| W15NH-T14α | strong |
| S16NH-W15α | strong |
| W18NH-E17α | strong |

TABLE S3-continued

List of the 40 sequential and intra-residue distance constraints used in the generation of the NMR ensemble.

| NOE cross-peaks | NOE strength |
|---|---|
| S19NH-W18α | strong |
| N12NH-Y11α | strong |
| W15NH-W15β | strong |
| W18NH-W18β | strong |
| T14NH-G13Hα1 | strong |
| T14NH-G13Hα2 | strong |
| W15NH-T14β | strong |
| Y11NH-G10α | strong |
| R8α-p9δ2 | strong |
| R8α-p9δ1 | strong |
| Y11NH-G10NH | strong |
| Y11δ-Y11NH | medium |
| Y11δ-N12NH | medium |
| V2NH-R1β | medium |
| R3NH-V2γ | medium |
| R5NH-V4γ | medium |
| W15α-Y15Hε3 | medium |
| W18α-W18Hε3 | medium |
| Y11β-N12NH | medium |
| T14NH-G13NH | medium |
| S16NH-W15β | weak |
| N12NH-N12δ | weak |
| S7β-R8NH | weak |
| W15Hε1-T14α | weak |
| W18Hε1-E17α | weak |
| G13α-T14γ | weak |
| G10NH-p9δ | weak |

Figure 10:
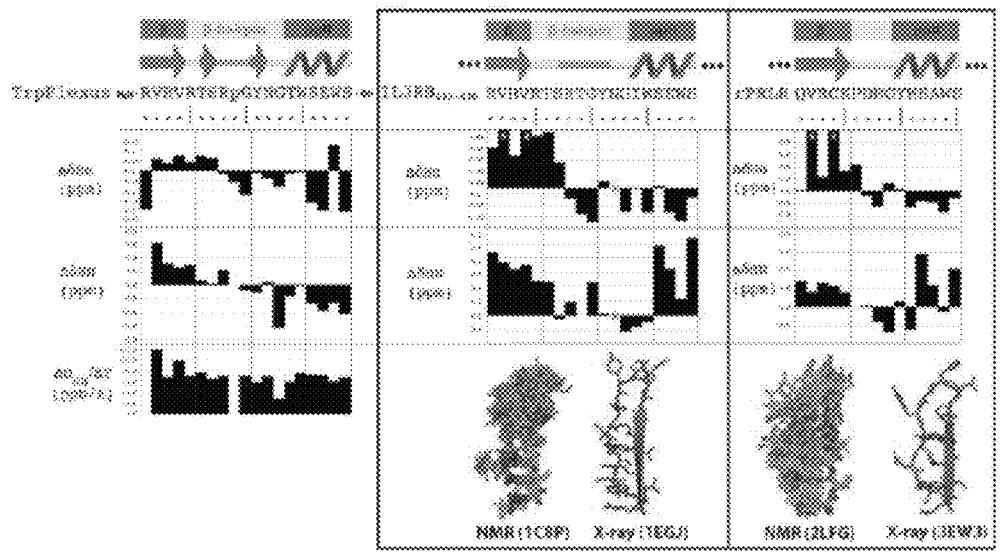
FIG. 10. Sequences, cartoon representations, and CSDs of Hα and HN backbone atoms for TrpPlexus as well as two WSXWS motifs found in Fn3 domains. For TrpPlexus the temperature coefficients presented for the backbone amides were calculated utilizing chemical shifts observed in TOCSY spectra obtained at 5° C., 25° C., and 45° C. which were least-squares fit to a linear equation. The slope of the least-squares fit line is the reported temperature coefficient. 3D representations can be seen comparing the X-ray and NMR structures of the Fn3 domains. White asterisks were added to indicate Hα CSDs larger than the y-axis maximum. A blue asterisk denotes an instance where data were not reported.

The resulting Hα chemical shift deviations (CSDs) from "random-coil" values were consistent in strength with those found in the CSDs of the WSXWS motifs in published NMR solution structures of whole Fn3 domains (PDBid(s): 2LFG, 1GCF, FIG. 10). However, relative to CSDs of the Hα protons observed for other mini-proteins, those found for TrpPlexus are relatively small. To obtain CD spectra and CSD values corresponding to a fully "folded control" sequence, a cyclic version of TrpPlexus was designed with a disulfide-bridge (V2→C, S19→C). The disulfide-bond formation of the cyclic TrpPlexus was monitored by analytical HPLC and ESI mass spectrometry (FIG. 5E) to identify a shift in the HPLC retention time and a reduction in mass for the cysteine sulfhydryl protons upon disulfide formation. The linear cysteine-containing sequence was observed to cyclize into two conformations. The major conformer was isolated using preparative HPLC and analyzed by NMR and CD spectroscopy. The long-range NOEs seen in FIG. 5D, the measured 3JHN-Hα scalar couplings, and Hα CSDs (FIG. 5C) were found to be in good agreement with the linear peptide. Furthermore, the CD characterizations of linear and disulfide-bridged structures were found to be nearly identical in strength and overall spectral shape (FIG. 4A,B). The similarity of both CD and NMR results strongly validates the structure and stability of the linear TrpPlexus as depicted in FIG. 5A.

Figure 6A:
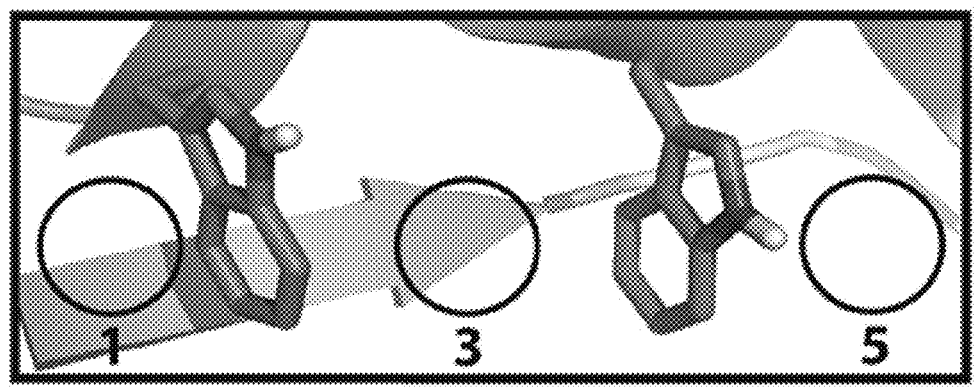
FIGS. 6A-6B. Near-UV CD thermal melts for the TrpPlexus cation-π interation network mutants. (6A) Schematic of the cation-π network of TrpPlexus detailing variable amino acid positions 1, 3, and 5 in the mutant sequences. (6B) Near-UV CD thermal melts for TrpPlexus ("RRR") and each mutant monitoring mean residue ellipticity at 280 nm (50 μM protein, 1 cm path length, 10 mM PBS buffer pH 7.5). Inset compares side-chain functionalities of the arginine (R), lysine (K), and L-citrulline (Cit) residues.
Figure 6B:
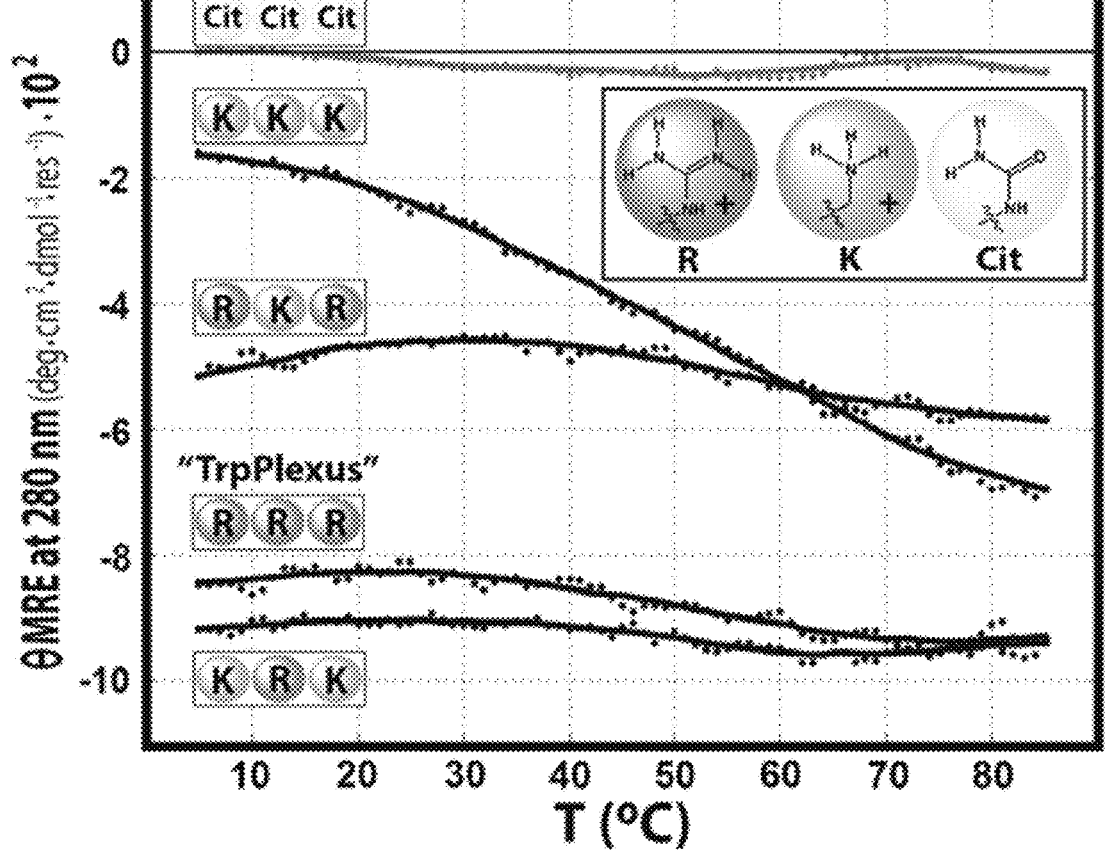
Figure 8:
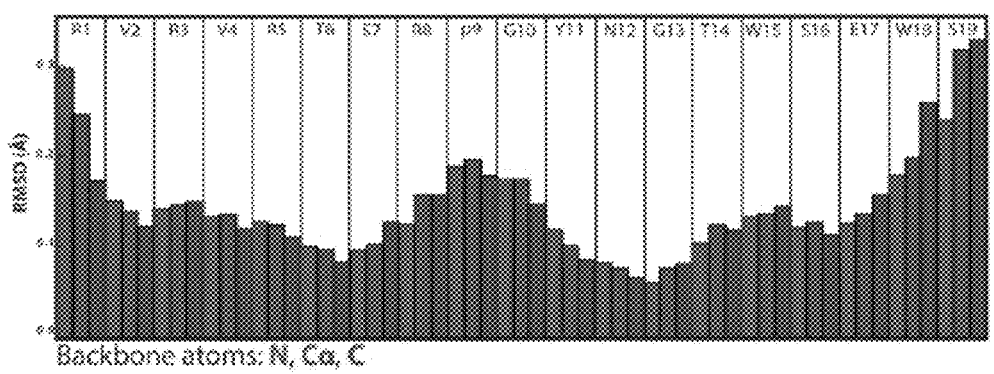
FIG. 8. RMSD(Å) to the lowest energy structure of the major backbone atoms (N, Cα, C) of each residue in the 25 NMR ensemble structures of the TrpPlexus mini-protein. This is a metric of relative structural variability.
Figure 9:
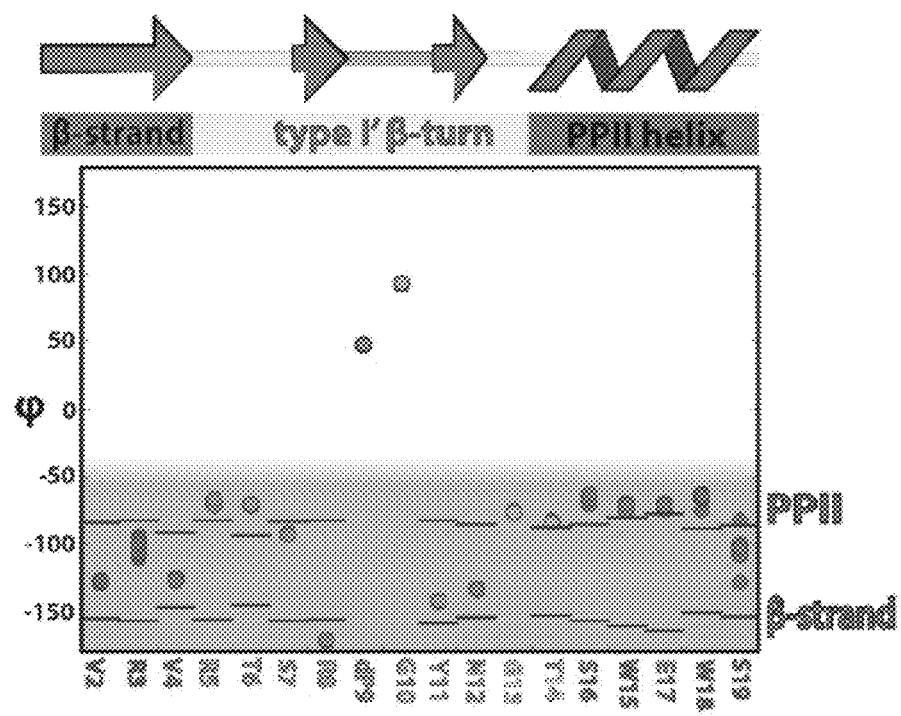
FIG. 9. TrpPlexus consensus secondary structure depiction and φ angle analysis of NMR solution structure. φ values for each residue are plotted for the NMR ensemble as well as two solutions to the Karplus equation for observed $^3J_{HN-H\alpha}$ values shown as horizontal black lines.

To explore the influence of cationic groups on fold stability, mutants were designed that replaced particular guanidinyl (arginine) side chain groups with either amino (lysine) cations or charge-neutral urea (L-citrulline) groups (FIG. 6). The near-UV CD signal monitored at 280 nm provides a metric of relative tertiary structure content (FIG. 6B). The absence of a strong near-UV CD signal for the L-citrulline triple mutant supports the conclusion that cation-π, and not stacking interactions or hydrogen bonding, is a primary determinant of TrpPlexus's folding. The near-UV CD signals, as a function of temperature, for TrpPlexus ("RRR") and the "KRK" mutant demonstrate weakly sigmoidal transitions to stronger ellipticities at elevated temperatures (FIG. 6). While being an important indicator of tertiary structure, the near-UV CD signal as a function of temperature is also dependent on local environmental factors. It is possible that the weak transitions are the result of small changes in the distributions of tryptophan and cationic side-chain rotamers at elevated temperatures. For the other cationic group mutants "RKR" and "KKK", the observed transitions in the ellipticities can similarly be attributed to fluctuations within rotamer populations since the cation-π interactions were stronger at elevated temperatures (20, 21). These data support a model in which a structure containing a β-hairpin is able to situate cationic and tryptophan residues on two adjacent peptide strands in proximity to one another. However, in order to achieve a discrete tertiary structure as opposed to a molten globule, a central arginine is required to interdigitate the two tryptophan residues, resulting in a gain of tertiary structure that enhances near-UV ellipticity. Thus, the central arginine residue is the critical determinant of tertiary structure as evidenced by near-UV CD signal strength.

Accordingly, the present inventors demonstrate herein that establishing a network of solvent-exposed cation-π interactions can be an effective strategy in the design of a novel miniature protein tertiary structure. The present inventors also validate a strategy in which solvent-exposed cation-π interactions serve as an alternative to hydrophobic-core packing as a protein design paradigm (16). Excising polypeptide sequences from protein structures having the following characteristics could prove valuable in the development of additional well-ordered mini-proteins: (1) rich in arginine and tryptophan side-chain tertiary contacts as well as contacts between the side chains of other residues containing cations (lysine and histidine) and π electron systems (phenylalanine and tyrosine), (2) secondary structure content supporting or enabling those contacts such as a β-hairpin, which can be stabilized and nucleated via canonical peptide design, and (3) an evolutionary conservation or homology between similar sequences maintaining a putative cation-π network. A plethora of small sequence motifs stabilized by cation-π interactions can be found in the Protein Databank. The present study demonstrates a successful workflow for miniprotein discovery initiated by bioinformatic sequence/structure analysis, followed by canonical peptide design stabilizing small secondary structure motifs, and validation via thorough structural characterization.

REFERENCES (1) Kortemme, T.; Ramirez-Alvarado, M.; Serrano, L. Science 1998, 281, 253-256.
(2) Struthers, M. D.; Cheng, R. P.; Imperiali, B. Science 1996, 271, 342-345.
(3) Neidigh, J. W.; Fesinmeyer, R. M.; Andersen, N. H. Nat. Struct. Biol. 2002, 9, 425-430.
(4) Honda, S.; Yamasaki, K.; Sawada, Y.; Morii, H. Structure 2004, 12, 1507-1518.
(5) Cochran, A. G.; Skelton, N. J.; Starovasnik, M. A. Proc. Natl. Acad. Sci. U.S.A 2001, 98, 5578-5583.
(6) Hodges, A. M.; Schepartz, A. J. Am. Chem. Soc. 2007, 129, 11024-11025.
(7) Espinosa, J. F.; Gellman, S. H. Angew. Chem., Int. Ed. 2000, 39, 2330-2333.
(8) Ottesen, J. J.; Imperiali, B. Nat. Struct. Biol. 2001, 8, 535-539.

(9) Kier, B. L.; Andersen, N. H. J. Am. Chem. Soc. 2008, 130, 14675-14683.
(10) Dougherty, D. A. Science 1996, 271, 163-168.
(11) Gallivan, J. P.; Dougherty, D. A. Proc. Natl. Acad. Sci. U.S.A 1999, 96, 9459-9464.
(12) Trotta, C. R.; Paushkin, S. V.; Patel, M.; Li, H.; Peltz, S. W. Nature 2006, 441, 375-377.
(13) Xiu, X.; Puskar, N. L.; Shanate, J. A. P.; Lester, H. A.; Dougherty, D. A. Nature 2009, 458, 534-537.
(14) Dagil, R.; Knudsen, M. J.; Olsen, J. G.; O'Shea, C.; Franzmann, M.; Goffin, V.; Teilum, K.; Breinholt, J.; Kragelund, B. B. Structure 2012, 20, 270-282.
(15) Hilton, D. J.; Watowich, S. S.; Katz, L.; Lodish, H. F. J. Biol. Chem. 1996, 271, 4699-4708.
(16) Gallivan, J. P.; Dougherty, D. A. J. Am. Chem. Soc. 2000, 122, 870-874.
(17) Shi, Z.; Olson, C.; Kallenbach, N. J. Am. Chem. Soc. 2002, 124, 3284-3291.
(18) Tatko, C. D.; Waters, M. L. Protein Sci. 2003, 12, 2443-2452.
(19) Hughes, R. M.; Waters, M. L. J. Am. Chem. Soc. 2006, 128, 12735-12742.
(20) Prajapati, R. S.; Sirajuddin, M.; Durani, V.; Sreeramulu, S.; Varadarajan, R. Biochemistry 2006, 45, 15000-15010.
(21) Chakravarty, S.; Varadarajan, R. Biochemistry 2002, 41, 8152-8161.
(22) Crooks, G. E.; Hon, G.; Chandonia, J. M.; Brenner, S. E. Genome Res. 2004, 14, 1188-1190.
(23) Bravo, J.; Staunton, D.; Heath, J.; Jones, E. EMBO J. 1998, 17, 1665-1674.
(24) Wang, X.; Rickert, M.; Garcia, K. Science 2005, 310, 1159-1163.
(25) Laporte, S. L.; Juo, Z. S.; Vaclavikova, J.; Colf, L. A.; Qi, X.; Heller, N. M.; Keegan, A. D.; Garcia, K. C. Cell 2008, 132, 259-272.
(26) Aritomi, M.; Kunishima, N.; Okamoto, T.; Kuroki, R.; Ota, Y.; Morikawa, K. Nature 1999, 401, 713-717.
(27) Syed, R. S.; Reid, S. W.; Li, C.; Cheetham, J. C.; Aoki, K. H.; Liu, B.; Zhan, H.; Osslund, T. D.; Chirino, A. J.; Zhang, J.; Finer-Moore, J.; Elliott, S.; Sitney, K.; Katz, B. A.; Matthews, D. J.; Wendoloski, J. J.; Egrie, J.; Stroud, R. M. Nature 1998, 395, 511-516.
(28) Tamada, T.; Honjo, E.; Maeda, Y.; Okamoto, T.; Ishibashi, M.; Tokunaga, M.; Kuroki, R. Proc. Natl. Acad. Sci. U.S.A 2006, 103, 3135-3140.
(29) Skiniotis, G.; Lupardus, P.; Martick, M.; Walz, T.; Garcia, K. C. Mol. Cell 2008, 31, 737-748.
(30) Rossjohn, J.; McKinstry, W. J.; Woodcock, J. M.; McClure, B. J.; Hercus, T. R.; Parker, M. W.; Lopez, A. F.; Bagley, C. J. Blood 2000, 95, 2491-2498.
(31) Broutin, I.; Jomain, J.; Tallet, E.; Agthoven, J.; Raynal, B.; Hoos, S.; Kragelund, B. B.; Kelly, P. A.; Ducruix, A.; England, P.; Goffin, V. J. Biol. Chem. 2010, 285, 8422-8433.
(32) Lupardus, P. J.; Birnbaum, M.; Garcia, K. Structure 2010, 18, 332-342.
(33) Varghese, J. N.; Moritz, R. L.; Lou, M. Z.; Donkelaar, A.; Ji, H.; Ivancic, N.; Branson, K. M.; Hall, N. E.; Simpson, R. J. Proc. Natl. Acad. Sci. U.S.A 2002, 99, 15959-15964.
(34) Huyton, T.; Zhang, J. G.; Luo, C. S.; Lou, M. Z.; Hilton, D. J.; Nicola, N. A.; Garrett, T. P. Proc. Natl. Acad. Sci. U.S.A 2007, 104, 12737-12742.
(35) Patino, E.; Kotzsch, A.; Saremba, S.; Nickel, J.; Schmitz, W.; Sebald, W.; Mueller, T. D. Structure 2011, 19, 1864-1875.
(36) Hamming, O. J.; Kang, L.; Svensson, A.; Karlsen, J. L.; Rahbek-Nielsen, H.; Paludan, S. R.; Hjorth, S. A.; Bondensgaard, K.; Hartmann, R. J. Biol. Chem. 2012, 287, 9454-9460.
(37) Carpenter, B.; Hemsworth, G. R.; Wu, Z.; Maamra, M.; Strasburger, C. J.; Ross, R. J.; Artymiuk, P. J. Structure 2012, 20, 487-497.
(38) Dunbrack, R. L.; Karplus, M. A. J. Mol. Biol. 1993, 230, 543-574.
(39) Leaver-Fay, A.; et al. An Object-Oriented Software Suite for the Simulation and Design of Macromolecules. In Methods in Enzymology; Johnson, M. L., Brand, L., Eds.; Computer Methods, Part C; Academic Press: New York, 2011; Vol. 487, pp 545-574.
(40) Vuister, G. W.; Bax, A. J. Am. Chem. Soc. 1993, 115, 7772-7777.
(41) Schwieters, C. D.; Kuszewski, J. J.; Tjandra, N.; Clore, G. M. J. Magn. Reson. 2003, 160, 66-74.
(42) Schwieters, C. D.; Kuszewski, J. J.; Clore, G. M. Prog. Nucl. Magn. Reson. Spectrosc. 2006, 48, 47-62.
(43) Within this report, the notation xy specifies a particular amino acid x at position number y in the 19 residue TrpPlexus sequence. Lowercase "p" denotes a D-Proline residue.
(44) Sedimentation equilibrium was conducted on the NMR sample used for solution structure determination.
(45) Kelly, S. M.; Price, N. C. Curr. Protein Pept. Sci. 2000, 4, 349-384.
(46) Horng, J. C.; Raines, R. T. Protein Sci. 2006, 1, 74-83.
(47) Chellgren, B. W.; Creamer, T. P. Biochemistry 2004, 43, 5864-5869.
(48) Krimm, S.; Tiffany, M. L. Isr. J. Chem. 1974, 12, 189-200.
(49) The lack of a significant exciton couplet in the far-UV CD spectra indicates that the indole rings of the tryptophan residues of TrpPlexus are not in a stacked or edge-to-face configuration. 5,9
(50) Brown, A. M.; Zondlo, N. J. Biochemistry 2012, 51, 5041-5051.
(51) p=0.54 for $\chi1/\chi2$ at $-66°/100°$ and $\varphi/\psi$ at $-90°/150°$. Strong W18Hδ1→W18HN and W15Hδ1→W15HN NOE cross-peaks were observed indicating the presence of this rotamer.
(52) Zheng, J.; Baghkhanian, A. M.; Nowick, J. S. J. Am. Chem. Soc. 2013, 135, 6846-6852.
(53) Nguyen, J. T.; Turck, C. W.; Cohen, F. E.; Zuckermann, R. N.; Lim, W. A. Science 1998, 282, 2088-2092.
(54) Bunagan, M. R.; Yang, X.; Saven, J. G.; Gai, F. J. Phys. Chem. B 2006, 110, 3759-3763.
(55) Appelbaum, J. M.; LaRochelle, J. R.; Smith, B. A.; Balkin, D. M.; Holub, J. M.; Schephartz, A. Chem. Biol. 2012, 19, 819-830.
(56) Smith, B.; Daniels, D. S.; Coplin, A.; Jordan, G.; McGregor, L.; Schepartz, A. J. Am. Chem. Soc. 2008, 130, 2948-2949.
(57) Li, M.; Tao, Y.; Shu, Y.; LaRochelle, J. R.; Steinauer, A.; Thompson, D.; Schepartz, A.; Chen, Z.-Y.; Liu, D. J. Am. Chem. Soc. 2015, 137, 14084-14093.

Various references are cited throughout this Specification, each of which is incorporated herein by reference in its entirety.

This invention may be embodied in other forms or carried out in other ways without departing from the spirit or essential characteristics thereof. The present disclosure is therefore to be considered as in all aspects illustrative and not restrictive of the scope of the invention being indicated by the appended claims, and all changes which come within the meaning and range of equivalency are intended to be embraced therein.

What is claimed is:

1. A miniature protein scaffold comprising:
   (a) Arg Val Arg Val Arg Thr Ser Arg Xaa Gly Tyr Asn Gly Thr Trp Ser Glu Trp Ser, wherein Xaa at position 9 is D-proline (D-Pro) and at least one of
   the arginine (Arg) at position 1, 5, or 8;
   the valine (Val) at position 2 or 4;
   the threonine (Thr) at position 6 or 14;
   the serine (Ser) at position 7, 16, or 19;
   the tyrosine (Tyr) at position 11;
   the asparagine (Asn) at position 12;
   the glycine (Gly) at position 13; and
   the glutamic acid (Glu) at position 17;
   is replaced by a different alpha amino acid; or
   (b) Arg Cys Arg Val Arg Thr Ser Arg D-Pro Gly Tyr Asn Gly Thr Trp Ser Glu Trp Cys, wherein at least one of
   the arginine (Arg) at position 1, 5, or 8;
   the valine (Val) at position 4;
   the threonine (Thr) at position 6 or 14;
   the serine (Ser) at position 7 or 16;
   the tyrosine (Tyr) at position 11;
   the asparagine (Asn) at position 12;
   the glycine (Gly) at position 13; and
   the glutamic acid (Glu) at position 17;
   is replaced by a different alpha amino acid.

2. The miniature protein scaffold of claim 1, wherein the cysteines (Cys) at positions 2 and 19 are linked via a disulfide bridge.

3. The miniature protein scaffold of claim 1, wherein the different alpha amino acid is selected from tyrosine (Tyr), glycine (Gly), phenylalanine (Phe), methionine (Met), alanine (Ala), serine (Ser), isoleucine (Ile), leucine (Leu), threonine (Thr), valine (Val), proline (Pro), lysine (Lys), histidine (His), glutamine (Gln), glutamic acid (Glu), tryptophan (Trp), arginine (Arg), aspartic acid (Asp), asparagine (Asn), and cysteine (Cys).

4. The miniature protein scaffold of claim 1, wherein the different alpha amino acid replacing Thr at position 14 is other than Ile.

5. The miniature protein scaffold of claim 1, wherein at least one of the threonine (Thr) at position 14 and the glutamic acid (Glu) at position 17 is replaced by the different alpha amino acid.

6. The miniature protein scaffold of claim 1, wherein at least one of the asparagine (Asn) at position 12 and the glycine (Gly) at position 13 are replaced by a different alpha amino acid that represents a conservative amino acid substitution or are not replaced by a different alpha amino acid.

7. The miniature protein scaffold of claim 1, wherein at least one of the arginine (Arg) at position 1 and at position 5 is replaced by lysine (Lys) or histidine (His).

8. The miniature protein scaffold of claim 1 comprising Arg Val Arg Val Arg Thr Ser Arg D-Pro Gly Tyr Asn Gly Ile Trp Ser Glu Trp Ser.

9. The miniature protein scaffold of claim 1 comprising Xaa Val Arg Val Xaa Thr Ser Arg D-Pro Gly Tyr Asn Gly Thr Trp Ser Glu Trp Ser, wherein Xaa at at least one of position 1 and position 5 is lysine (Lys) or histidine (His).

10. The miniature protein scaffold of claim 1 comprising Arg Cys Arg Val Arg Thr Ser Arg D-Pro Gly Tyr Asn Gly Ile Trp Ser Glu Trp Cys.

11. The miniature protein scaffold of claim 1 comprising Xaa Cys Arg Val Xaa Thr Ser Arg D-Pro Gly Tyr Asn Gly Thr Trp Ser Glu Trp Cys, wherein Xaa at at least one of position 1 and position 5 is lysine (Lys) or histidine (His).

12. The miniature protein scaffold of claim 1, wherein at least one amino acid residue of the miniature protein scaffold is post-translationally modified.

13. The miniature protein scaffold of claim 12, wherein the at least one amino acid residue is glycosylated, phosphorylated, and/or methylated.

14. The miniature protein scaffold of claim 1, consisting essentially of:
 (a) Arg Val Arg Val Arg Thr Ser Arg Xaa Gly Tyr Asn Gly Thr Trp Ser Glu Trp Ser, wherein Xaa at position 9 is D-proline (D-Pro) and at least one of
  the arginine (Arg) at position 1, 5, or 8;
  the valine (Val) at position 2 or 4;
  the threonine (Thr) at position 6 or 14;
  the serine (Ser) at position 7, 16, or 19;
  the tyrosine (Tyr) at position 11;
  the asparagine (Asn) at position 12;
  the glycine (Gly) at position 13; and
  the glutamic acid (Glu) at position 17;
 is replaced by a different alpha amino acid; or
 (b) Arg Cys Arg Val Arg Thr Ser Arg D-Pro Gly Tyr Asn Gly Thr Trp Ser Glu Trp Cys, wherein at least one of
  the arginine (Arg) at position 1, 5, or 8;
  the valine (Val) at position 4;
  the threonine (Thr) at position 6 or 14;
  the serine (Ser) at position 7 or 16;
  the tyrosine (Tyr) at position 11;
  the asparagine (Asn) at position 12;
  the glycine (Gly) at position 13; and
  the glutamic acid (Glu) at position 17;
 is replaced by a different alpha amino acid.

15. The miniature protein scaffold of claim 1, consisting of:
 (a) Arg Val Arg Val Arg Thr Ser Arg Xaa Gly Tyr Asn Gly Thr Trp Ser Glu Trp Ser, wherein Xaa at position 9 is D-proline (D-Pro) and at least one of
  the arginine (Arg) at position 1, 5, or 8;
  the valine (Val) at position 2 or 4;
  the threonine (Thr) at position 6 or 14;
  the serine (Ser) at position 7, 16, or 19;
  the tyrosine (Tyr) at position 11;
  the asparagine (Asn) at position 12;
  the glycine (Gly) at position 13; and
  the glutamic acid (Glu) at position 17;
 is replaced by a different alpha amino acid; or
 (b) Arg Cys Arg Val Arg Thr Ser Arg D-Pro Gly Tyr Asn Gly Thr Trp Ser Glu Trp Cys, wherein at least one of
  the arginine (Arg) at position 1, 5, or 8;
  the valine (Val) at position 4;
  the threonine (Thr) at position 6 or 14;
  the serine (Ser) at position 7 or 16;
  the tyrosine (Tyr) at position 11;
  the asparagine (Asn) at position 12;
  the glycine (Gly) at position 13; and
  the glutamic acid (Glu) at position 17;
 is replaced by a different alpha amino acid.

* * * * *

SEQUENCE LISTING

<160> NUMBER OF SEQ ID NOS: 9

<210> SEQ ID NO 1
<211> LENGTH: 19
<212> TYPE: PRT
<213> ORGANISM: Artificial Sequence
<220> FEATURE:
<223> OTHER INFORMATION: protein scaffold
<220> FEATURE:
<221> NAME/KEY: VARIANT
<222> LOCATION: (9)..(9)
<223> OTHER INFORMATION: X can be Pro

<400> SEQUENCE: 1

Arg Val Arg Val Arg Thr Ser Arg Xaa Gly Tyr Asn Gly Thr Trp Ser
1               5                   10                  15

Glu Trp Ser

<210> SEQ ID NO 2
<211> LENGTH: 19
<212> TYPE: PRT
<213> ORGANISM: Artificial sequence
<220> FEATURE:
<223> OTHER INFORMATION: protein scaffold

<400> SEQUENCE: 2

Arg Val Arg Val Arg Thr Ser Arg Pro Gly Tyr Asn Gly Thr Trp Ser
1               5                   10                  15

Glu Trp Ser

<210> SEQ ID NO 3
<211> LENGTH: 19
<212> TYPE: PRT
<213> ORGANISM: Artificial sequence
<220> FEATURE:
<223> OTHER INFORMATION: protein scaffold
<220> FEATURE:
<221> NAME/KEY: VARIANT
<222> LOCATION: (1)..(1)
<223> OTHER INFORMATION: X can be Arg or any alpha amino acid
<220> FEATURE:
<221> NAME/KEY: VARIANT
<222> LOCATION: (2)..(2)
<223> OTHER INFORMATION: X can be Val or any alpha amino acid
<220> FEATURE:
<221> NAME/KEY: VARIANT
<222> LOCATION: (4)..(4)
<223> OTHER INFORMATION: X can be Val or any alpha amino acid
<220> FEATURE:
<221> NAME/KEY: VARIANT
<222> LOCATION: (5)..(5)
<223> OTHER INFORMATION: X can be Arg or any alpha amino acid
<220> FEATURE:
<221> NAME/KEY: VARIANT
<222> LOCATION: (6)..(6)
<223> OTHER INFORMATION: X can be Thr or any alpha amino acid
<220> FEATURE:
<221> NAME/KEY: VARIANT
<222> LOCATION: (7)..(7)
<223> OTHER INFORMATION: X can be Ser or any alpha amino acid
<220> FEATURE:
<221> NAME/KEY: VARIANT
<222> LOCATION: (8)..(8)
<223> OTHER INFORMATION: X can be Arg or any alpha amino acid
<220> FEATURE:
<221> NAME/KEY: VARIANT
<222> LOCATION: (11)..(11)
<223> OTHER INFORMATION: X can be Tyr or any alpha amino acid
<220> FEATURE:
<221> NAME/KEY: VARIANT
<222> LOCATION: (12)..(12)
<223> OTHER INFORMATION: X can be Asn or any alpha amino acid

```
<220> FEATURE:
<221> NAME/KEY: VARIANT
<222> LOCATION: (13)..(13)
<223> OTHER INFORMATION: X can be Gly or any alpha amino acid
<220> FEATURE:
<221> NAME/KEY: VARIANT
<222> LOCATION: (14)..(14)
<223> OTHER INFORMATION: X can be Thr or any alpha amino acid
<220> FEATURE:
<221> NAME/KEY: VARIANT
<222> LOCATION: (16)..(16)
<223> OTHER INFORMATION: X can be Ser or any alpha amino acid
<220> FEATURE:
<221> NAME/KEY: VARIANT
<222> LOCATION: (17)..(17)
<223> OTHER INFORMATION: X can be Glu or any alpha amino acid
<220> FEATURE:
<221> NAME/KEY: VARIANT
<222> LOCATION: (19)..(19)
<223> OTHER INFORMATION: X can be Ser or any alpha amino acid

<400> SEQUENCE: 3

Xaa Xaa Arg Xaa Xaa Xaa Xaa Xaa Pro Gly Xaa Xaa Xaa Xaa Trp Xaa
1               5                   10                  15

Xaa Trp Xaa

<210> SEQ ID NO 4
<211> LENGTH: 19
<212> TYPE: PRT
<213> ORGANISM: Artificial Sequence
<220> FEATURE:
<223> OTHER INFORMATION: protein scaffold

<400> SEQUENCE: 4

Arg Cys Arg Val Arg Thr Ser Arg Pro Gly Tyr Asn Gly Thr Trp Ser
1               5                   10                  15

Glu Trp Cys

<210> SEQ ID NO 5
<211> LENGTH: 19
<212> TYPE: PRT
<213> ORGANISM: Artificial sequence
<220> FEATURE:
<223> OTHER INFORMATION: protein scaffold
<220> FEATURE:
<221> NAME/KEY: VARIANT
<222> LOCATION: (1)..(1)
<223> OTHER INFORMATION: X can be Arg or any alpha amino acid
<220> FEATURE:
<221> NAME/KEY: VARIANT
<222> LOCATION: (4)..(4)
<223> OTHER INFORMATION: X can be Val or any alpha amino acid
<220> FEATURE:
<221> NAME/KEY: VARIANT
<222> LOCATION: (5)..(5)
<223> OTHER INFORMATION: X can be Arg or any alpha amino acid
<220> FEATURE:
<221> NAME/KEY: VARIANT
<222> LOCATION: (6)..(6)
<223> OTHER INFORMATION: X can be Thr or any alpha amino acid
<220> FEATURE:
<221> NAME/KEY: VARIANT
<222> LOCATION: (7)..(7)
<223> OTHER INFORMATION: X can be Ser or any alpha amino acid
<220> FEATURE:
<221> NAME/KEY: VARIANT
<222> LOCATION: (8)..(8)
<223> OTHER INFORMATION: X can be Arg or any alpha amino acid
<220> FEATURE:
<221> NAME/KEY: VARIANT
<222> LOCATION: (11)..(11)
<223> OTHER INFORMATION: X can be Tyr or any alpha amino acid
```

-continued

```
<220> FEATURE:
<221> NAME/KEY: VARIANT
<222> LOCATION: (12)..(12)
<223> OTHER INFORMATION: X can be Asn or any alpha amino acid
<220> FEATURE:
<221> NAME/KEY: VARIANT
<222> LOCATION: (13)..(13)
<223> OTHER INFORMATION: X can be Gly or any alpha amino acid
<220> FEATURE:
<221> NAME/KEY: VARIANT
<222> LOCATION: (14)..(14)
<223> OTHER INFORMATION: X can be Thr or any alpha amino acid
<220> FEATURE:
<221> NAME/KEY: VARIANT
<222> LOCATION: (16)..(16)
<223> OTHER INFORMATION: X can be Ser or any alpha amino acid
<220> FEATURE:
<221> NAME/KEY: VARIANT
<222> LOCATION: (17)..(17)
<223> OTHER INFORMATION: X can be Glu or any alpha amino acid

<400> SEQUENCE: 5

Xaa Cys Arg Xaa Xaa Xaa Xaa Pro Gly Xaa Xaa Xaa Xaa Trp Xaa
1               5                   10                  15

Xaa Trp Cys

<210> SEQ ID NO 6
<211> LENGTH: 19
<212> TYPE: PRT
<213> ORGANISM: Artificial sequence
<220> FEATURE:
<223> OTHER INFORMATION: protein scaffold
<220> FEATURE:
<221> NAME/KEY: VARIANT
<222> LOCATION: (14)..(14)
<223> OTHER INFORMATION: X is Thr or Ile

<400> SEQUENCE: 6

Arg Val Arg Val Arg Thr Ser Arg Pro Gly Tyr Asn Gly Xaa Trp Ser
1               5                   10                  15

Glu Trp Ser

<210> SEQ ID NO 7
<211> LENGTH: 19
<212> TYPE: PRT
<213> ORGANISM: Artificial Sequence
<220> FEATURE:
<223> OTHER INFORMATION: protein scaffold
<220> FEATURE:
<221> NAME/KEY: VARIANT
<222> LOCATION: (1)..(1)
<223> OTHER INFORMATION: X is Lys or His
<220> FEATURE:
<221> NAME/KEY: VARIANT
<222> LOCATION: (5)..(5)
<223> OTHER INFORMATION: X is Lys or His

<400> SEQUENCE: 7

Xaa Val Arg Val Xaa Thr Ser Arg Pro Gly Tyr Asn Gly Thr Trp Ser
1               5                   10                  15

Glu Trp Ser

<210> SEQ ID NO 8
<211> LENGTH: 19
<212> TYPE: PRT
<213> ORGANISM: Artificial Sequence
<220> FEATURE:
<223> OTHER INFORMATION: protein scaffold
```

```
<220> FEATURE:
<221> NAME/KEY: VARIANT
<222> LOCATION: (14)..(14)
<223> OTHER INFORMATION: X is Thr or Ile

<400> SEQUENCE: 8

Arg Cys Arg Val Arg Thr Ser Arg Pro Gly Tyr Asn Gly Xaa Trp Ser
1               5                   10                  15

Glu Trp Cys

<210> SEQ ID NO 9
<211> LENGTH: 19
<212> TYPE: PRT
<213> ORGANISM: Artificial sequence
<220> FEATURE:
<223> OTHER INFORMATION: protein scaffold
<220> FEATURE:
<221> NAME/KEY: VARIANT
<222> LOCATION: (1)..(1)
<223> OTHER INFORMATION: X is Lys or His
<220> FEATURE:
<221> NAME/KEY: VARIANT
<222> LOCATION: (5)..(5)
<223> OTHER INFORMATION: X is Lys or His

<400> SEQUENCE: 9

Xaa Cys Arg Val Xaa Thr Ser Arg Pro Gly Tyr Asn Gly Thr Trp Ser
1               5                   10                  15

Glu Trp Cys
```